US011380421B2

(12) United States Patent
Chiu et al.

(10) Patent No.: US 11,380,421 B2
(45) **Date of Patent: *Jul. 5, 2022**

(54) PATHOGEN DETECTION USING NEXT GENERATION SEQUENCING

(71) Applicant: The Regents of the University of California, Oakland, CA (US)

(72) Inventors: Charles Chiu, San Francisco, CA (US); Samia Naccache, San Francisco, CA (US); Scot Federman, Portola Valley, CA (US); Doug Stryke, Albany, CA (US); Steve Miller, San Mateo, CA (US); Erik Samayoa, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,487

(22) Filed: May 13, 2020

(65) Prior Publication Data

US 2020/0335177 A1 Oct. 22, 2020

Related U.S. Application Data

(63) Continuation of application No. 15/917,286, filed on Mar. 9, 2018, which is a continuation of application No. PCT/US2016/052912, filed on Sep. 21, 2016.

(60) Provisional application No. 62/221,574, filed on Sep. 21, 2015.

(51) Int. Cl.
*G16B 30/10* (2019.01)
*G16B 30/00* (2019.01)
*G16B 20/00* (2019.01)
*G16B 20/20* (2019.01)

(52) U.S. Cl.
CPC ............. *G16B 30/10* (2019.02); *G16B 20/00* (2019.02); *G16B 20/20* (2019.02); *G16B 30/00* (2019.02)

(58) Field of Classification Search
None
See application file for complete search history.

(56) References Cited

U.S. PATENT DOCUMENTS

2009/0150084 A1 6/2009 Colwell et al.
2016/0342737 A1* 11/2016 Kaye ..................... G06T 11/206

FOREIGN PATENT DOCUMENTS

CN 102154450 A 8/2011
WO 2012/101643 A1 8/2012

OTHER PUBLICATIONS

Muhl et al. Activity and DNA contamination of commercial polymerase chain reaction reagents for the universal 16S rDNA real-time polymerase chain reaction detection of bacterial pathogens in blood Diagnostic Microbiology and Infectious Disease vol. 66, pp. 41-49 (Year: 2010).*
Yang et al. Quantitative Multiprobe PCR Assay for simultaneous Detection and Identification to Species Level of Bacterial Pathogens Journal of Clinical Microbiology vol. 40, pp. 3449-3454 (Year: 2002).*
Huson et al. MEGAN analysis of metagenomic data Genome Research vol. 17, pp. 377-386 (Year: 2007).*
Wilson et al. Actionable Diagnosis of Neuroleptospirosis by Next-Generation Sequencing The New England Journal of Medicine vol. 370, pp. 2408-2417 (Year: 2014).*
Flicek et al. Sense from sequence reads: methods for alignment and assembly Nature Methods vol. 6 pp. S6-S12 (Year: 2009).*
Gouba et al. Plant and Fungal Diversity in Gut Microbiota as Revealed by Molecular and Culture Investigations PLOS ONE vol. 8 artivle e59474 (Year: 2013).*
Shendure et al. Next-generation DNA sequencing Nature Biotechnology vol. 26, pp. 1135-1145 (Year: 2008).*
Zaharia Faster and More Accurate Sequence Alignment with SNAP arXiv:1111.5572v1 [cs.DS] (Year: 2011).*
Li et al. 2008 SOAP: short oligonucleotide alignment program Bioinformatics vol. 24, pp. 713-714 (Year: 2008).*
Li et al. 2009 SOAP2: an improved ultrafast tool for short read alignment Bioinformatics vol. 25, pp. 1966-1967 (Year: 2009).*
Carver et al. BamView: visualizing and interpretation of next-generation sequencing read alignments Briefings in Bioinformatics vol. 14, pp. 203-212 (Year: 2012).*
Bankwitz, Robert, Extended European Search Report, European Patent Office, Application No. 16849519.0, dated Apr. 30, 2019.
Droge et al., "Taxonomic binning of metagenome samples generated by next-generation sequencing technologies", Briefings in Bioinformatics, vol. 13, No. 6, Jul. 31, 2012, pp. 646-655.
Kostic et al., "Pathseq: software to identify or discover microbes by deep sequencing of human tissue," Nature Biotechnology, vol. 29, No. 5, pp. 393-396, May 2011.

(Continued)

*Primary Examiner* — John S Brusca
(74) *Attorney, Agent, or Firm* — Gavrilovich, Dodd & Lindsey LLP

(57) ABSTRACT

Embodiments are directed to systems and methods for pathogen detection using next-generation sequencing (NGS) analysis of a sample. Embodiments may apply alignment algorithms (e.g., SNAP and/or RAPSearch alignment algorithms) to align individual sequence reads from a sample in a next-generation sequencing (NGS) dataset against reference genome entries in a classified reference genome database. Embodiments of the present invention may include classifying, filtering, and displaying results to a clinician that can then quickly and easily obtain the results of the sequencing to identify a pathogen or other genetic material in a sample that is being tested. A negative sample and a corresponding database can be used to remove contaminants from a list of candidate pathogens. Thus, embodiments are directed to a system that is configured to filter the results of a sequencing alignment and classify a sample quickly.

12 Claims, 14 Drawing Sheets

Specification includes a Sequence Listing.

(56) References Cited

OTHER PUBLICATIONS

Naccache et al., "A cloud-compatible bioinformatics pipeline for ultrarapid pathogen identification from next-generation sequencing of clinical samples," Genome Res., vol. 24, No. 7, pp. 1180-1192, Jul. 2014.

International Search Report and Written Opinion from PCT/US2016/052912, dated Mar. 20, 2017.

* cited by examiner 620 630 640 610 650

| Sequencing Stats | | | |
|---|---|---|---|
| Read Type: | #1 (EV-D68) | #2 (EV-D68) | #3 (neg control) |
| Raw Data | 2,159,196 | 2,285,044 | 2,768,551 |
| Preprocessed | 1,933,046 | 2,063,026 | 2,619,804 |
| Human Matched | 1,725,425 | 1,980,081 | 2,440,235 |
| Human Unmatched | 207,621 | 82,945 | 179,569 |
| NT Matched | 133,932 | 10,689 | 101,423 |
| NT Virus Matched | 133,827 | 10,581 | 92,458 |
| NT Bacteria Matched | 21 | 21 | 8,302 |
| | | | |
| % Human | 89.3 | 96.0 | 93.1 |
| % Preprocessed | 89.5 | 90.3 | 94.6 |

*FIG. 6*

No filtering or Classification

700

710 720 730 740 750 760 770

| Species | Genus | Family | Tag | #1(EV-D68) | #2(Ev-D68) | #3(neg control) |
|---|---|---|---|---|---|---|
| Hepatitis C virus | Hepacivirus | Flaviviridae | Host-01\|human\|vertebrates; | 0 | 0 | 92252 |
| Hepatitis B virus | Orthohepadnavirus | Hepadnaviridae | Host-01\|human\|vertebrates; | 0 | 0 | 1 |
| Enterovirus D | Enterovirus | Picornaviridae | Host-01\|human\|vertebrates; | 133004 | 10385 | 0 |
| Enterovirus sp. | Enterovirus | Picornaviridae | Host-01\|human\|vertebrates; | 247 | 93 | 0 |
| Human enterovirus | Enterovirus | Picornaviridae | Host-01\|human\|vertebrates; | 574 | 102 | 0 |
| Human enterovirus K1105_171204 | Enterovirus | Picornaviridae | Host-01\|human\|vertebrates; | 1 | 0 | 0 |
| Human rhinovirus sp. | Enterovirus | Picornaviridae | Host-01\|human\|vertebrates; | 1 | 0 | 0 |
| Simian virus 40 | Enterovirus | Picornaviridae | Host-01\|human\|vertebrates; | 0 | 1 | 0 |
| Cactus virus X | Polyomavirus | Polyomaviridae | Host-17\|plants; | 0 | 0 | 1 |
| Enterobacteria phage M13 | Potexvirus | Alphaflexiviridae | Host-19\|bacteria; | 0 | 0 | 185 |
| Enterobacteria phage f1 | Inovirus | Inoviridae | Host-19\|bacteria; | 0 | 0 | 7 |
| Enterobacteria phage T7 | Inovirus | Inoviridae | Host-19\|bacteria; | 0 | 0 | 3 |
| Yersinia phage phiA1122 | T7likevirus | Poloviridae | Host-19\|bacteria; | 0 | 0 | 4 |
| Proprionibacterium phageATCC29399B_C | T7likevirus | Siphoviridae | Host-19\|bacteria; | 0 | 0 | 1 |
| Staphylococcus phage StB12 | | Siphoviridae | Host-19\|bacteria; | 0 | 0 | 2 |
| Staphylococcus phage StB27 | | Siphoviridae | Host-19\|bacteria; | 0 | 0 | 2 |

Filtering but No Classification

800

| [0001] Species | Genus | Family | Tag | #1(EV-D68) | #2(EV-D68) | #3(neg-control) |
|---|---|---|---|---|---|---|
| Hepatitis C virus | Hepacivirus | Flaviviridae | Host-01\|human\|vertebrates; | 0 | 0 | 81989 |
| Enterovirus D | Enterovirus | Picornaviridae | Host-01\|human\|vertebrates; | 130566 | 10027 | 0 |
| Enterovirus sp. | Enterovirus | Picornaviridae | Host-01\|human\|vertebrates; | 245 | 92 | 0 |
| Human enterovirus | Enterovirus | Picornaviridae | Host-01\|human\|vertebrates; | 568 | 101 | 0 |
| Human enterovirus K1105_17 | Enterovirus | Picornaviridae | Host-01\|human\|vertebrates; | 1 | 0 | 0 |
| Human rhinovirus sp. | Enterovirus | Picornaviridae | Host-01\|human\|vertebrates; | 1 | 0 | 0 |
| Cactus virus X | Potexvirus | Alphaflexiviridae | Host-17\|plants; | 0 | 0 | 1 |
| Enterobacteria phage M13 | Inovirus | Inoviridae | Host-19\|bacteria; | 0 | 0 | 176 |
| Enterobacteria phage f1 | Inovirus | Inoviridae | Host-19\|bacteria; | 0 | 0 | 6 |
| Enterobacteria phage T7 | T7likevirus | Podoviridae | Host-19\|bacteria; | 0 | 0 | 3 |
| Yersinia phage phiA1122 | T7likevirus | Podoviridae | Host-19\|bacteria; | 0 | 0 | 4 |
| Propionibacterium phage ATCC29399B_C | | Siphoviridae | Host-19\|bacteria; | 0 | 0 | 1 |
| Staphylococcus phage StB12 | | Siphoviridae | Host-19\|bacteria; | 0 | 0 | 2 |
| Staphylococcus phage StB27 | | Siphoviridae | Host-19\|bacteria; | 0 | 0 | 2 |

FIG. 8

Classification but no Filtering

900

<table>
<tr><th>Species</th><th>Genus</th><th>Family</th><th>Tag</th><th>#1(EV-D68)</th><th>#2(EV-D68)</th><th>#3(neg-control)</th></tr>
<tr><td>*</td><td>*</td><td>*</td><td>Host-01|human|vertebrates;</td><td>0</td><td>0</td><td>129</td></tr>
<tr><td>*</td><td>*</td><td>Flaviviridae</td><td>Host-01|human|vertebrates;</td><td>0</td><td>0</td><td>1</td></tr>
<tr><td>Hepatitis C virus</td><td>Hepacivirus</td><td>Flaviviridae</td><td>Host-01|human|vertebrates;</td><td>0</td><td>0</td><td>92122</td></tr>
<tr><td>Hepatitis B virus</td><td>Orthohepadnavirus</td><td>Hepadnaviridae</td><td>Host-01|human|vertebrates;</td><td>0</td><td>0</td><td>1</td></tr>
<tr><td>*</td><td>Enterovirus</td><td>Picornaviridae</td><td>Host-01|human|vertebrates;</td><td>10461</td><td>2561</td><td>0</td></tr>
<tr><td>Enterovirus D</td><td>Enterovirus</td><td>Picornaviridae</td><td>Host-01|human|vertebrates;</td><td>123349</td><td>8016</td><td>0</td></tr>
<tr><td>Enterovirus sp.</td><td>Enterovirus</td><td>Picornaviridae</td><td>Host-01|human|vertebrates;</td><td>15</td><td>2</td><td>0</td></tr>
<tr><td>Human enterovirus</td><td>Enterovirus</td><td>Picornaviridae</td><td>Host-01|human|vertebrates;</td><td>2</td><td>1</td><td>0</td></tr>
<tr><td>Simian virus 40</td><td>Polyomavirus</td><td>Polyomaviridae</td><td>Host-01|human|vertebrates;</td><td>0</td><td>1</td><td>0</td></tr>
<tr><td>Cactus virus X</td><td>Potexvirus</td><td>Alphaflexiviridae</td><td>Host-17|plants;</td><td>0</td><td>0</td><td>1</td></tr>
<tr><td>*</td><td>*</td><td>*</td><td>Host-19|bacteria;</td><td>0</td><td>0</td><td>180</td></tr>
<tr><td>Enterobacteria phage</td><td>Inovirus</td><td>Inoviridae</td><td>Host-19|bacteria;</td><td>0</td><td>0</td><td>12</td></tr>
<tr><td>*</td><td>T7likevirus</td><td>Podoviridae</td><td>Host-19|bacteria;</td><td>0</td><td>0</td><td>4</td></tr>
<tr><td>Enterobacteria phage</td><td>T7likevirus</td><td>Podoviridae</td><td>Host-19|bacteria;</td><td>0</td><td>0</td><td>3</td></tr>
<tr><td colspan="2">Propionibacterium phage ATCC29399B_C</td><td>Siphoviridae</td><td>Host-19|bacteria;</td><td>0</td><td>0</td><td>1</td></tr>
<tr><td colspan="2">Staphylococcus phage StB12</td><td>Siphoviridae</td><td>Host-19|bacteria;</td><td>0</td><td>0</td><td>2</td></tr>
<tr><td colspan="2">Staphylococcus phage StB27</td><td>Siphoviridae</td><td>Host-19|bacteria;</td><td>0</td><td>0</td><td>2</td></tr>
</table>

FIG. 9

Results after applying classification and filtering algorithms

1000

| Species | Genus | Family | Tag | #1(EV-D68) | #2(EV-D68) | #3(neg-control) |
|---|---|---|---|---|---|---|
| * | * | * | Host-01\|human\|vertebrates; | 0 | 0 | 120 |
| * | * | Flaviviridae | Host-01\|human\|vertebrates; | 0 | 0 | 1 |
| Hepatitis C virus | Hepacivirus | Flaviviridae | Host-01\|human\|vertebrates; | 0 | 0 | 81868 |
| * | Enterovirus | Picornaviridae | Host-01\|human\|vertebrates; | 10174 | 2532 | 0 |
| Enterovirus D | Enterovirus | Picornaviridae | Host-01\|human\|vertebrates; | 121190 | 7685 | 0 |
| Enterovirus sp. | Enterovirus | Picornaviridae | Host-01\|human\|vertebrates; | 15 | 2 | 0 |
| Human enterovirus | Enterovirus | Picornaviridae | Host-01\|human\|vertebrates; | 2 | 1 | 0 |
| Cactus virus X | Potexvirus | Alphaflexiviridae | Host-17\|plants; | 0 | 0 | 1 |
| * | * | * | Host-19\|bacteria; | 0 | 0 | 173 |
| Enterobacteria phageM13 | Inovirus | Inoviridae | Host-19\|bacteria; | 0 | 0 | 9 |
| * | T7likevirus | Podoviridae | Host-19\|bacteria; | 0 | 0 | 4 |
| Enterobacteria phage T7 | T7likevirus | Podoviridae | Host-19\|bacteria; | 0 | 0 | 3 |
| Propionibacterium phage ATCC29399B_C | | Siphoviridae | Host-19\|bacteria; | 0 | 0 | 1 |
| Staphylococcus phage StB12 | | Siphoviridae | Host-19\|bacteria; | 0 | 0 | 2 |
| Staphylococcus phage StB27 | | Siphoviridae | Host-19\|bacteria; | 0 | 0 | 2 |

| [0001] Sample Description | DNA/RNA library | % Reads Passing Quality Control | # of Raw Reads | # of Reads after Quality Filtering and Adapter Trimming | # of Reads Aligned to Human/Primate | # of Non-Human/ Primate Reads | % Human/ Primate Reads | # of Reads Aligned to NCBI NT database |
|---|---|---|---|---|---|---|---|---|
| No Template Control (NTC) | DNA | 84.3 | 6,664,047 | 5,619,424 | 539,093 | 5,080,331 | 9.6 | 3,848,762 |
| No Template Control (NTC) | RNA | 59.1 | 13,243,517 | 7,829,946 | 2,174,615 | 5,655,331 | 27.8 | 3,065,872 |
| External Positive Control (PC)* | DNA | 62.9 | 15,488,998 | 9,735,493 | 9,154,273 | 581,220 | 94.0 | 469,147 |
| External Positive Control (PC)* | RNA | 64.8 | 6,841,850 | 4,433,299 | 1,550,481 | 2,882,818 | 35.0 | 1,616,732 |
| Analytical Sample | DNA | 67.8 | 23,638,587 | 16,037,745 | 15,999,078 | 38,667 | 99.8 | 24,156 |
| Analytical Sample | RNA | 80.8 | 9,161,626 | 7,400,632 | 5,635,904 | 1,764,728 | 76.2 | 889,944 |

*7 organism positive control mixture of CMV, HIV, *Streptococcus agalactiae, Klebsiella pneumoniae, Cryptococcus neoformans, Aspergillus niger,* and *Toxoplasma gondii*

Abbreviations: NTC, no template control; PC, positive control; NCBI, National Center for Biotechnology Information, NT, nucleotide

| [0001] Species | Genus | Family | Host | DNA NTC | RNA NTC | DNA PC | RNA PC | DNA Patient CSF | RNA Patient CSF |
|---|---|---|---|---|---|---|---|---|---|
| Human mastadenovirus F | Mastadenovirus | Adenoviridae | Human\|vertebrates | 0 | 68 | 0 | 0 | 0 | 0 |
| GB virus C | Pegivirus | Flaviviridae | Human\|vertebrates | 0 | 0 | 0 | 1,406 | 0 | 2 |
| Cercopithecine herpesvirus 5 | Cytomegalovirus | Herpesviridae | Human\|vertebrates | 0 | 32 | 0 | 0 | 0 | 0 |
| Human herpesvirus 5 | Cytomegalovirus | Herpesviridae | Human\|vertebrates | 0 | 0 | 3,026 | 0 | 0 | 0 |
| Declassified | Declassified | Papillomaviridae | Human\|vertebrates | 1 | 0 | 0 | 0 | 0 | 0 |
| Alphapapillomavirus 2 | Alphapapillomavirus | Papillomaviridae | Human\|vertebrates | 39 | 16 | 0 | 0 | 0 | 0 |
| Betapapillomavirus 1 | Betapapillomavirus | Papillomaviridae | Human\|vertebrates | 0 | 30 | 0 | 0 | 0 | 0 |
| Betapapillomavirus 2 | Betapapillomavirus | Papillomaviridae | Human\|vertebrates | 0 | 0 | 0 | 0 | 0 | 72 |
| * | Lentivirus | Retroviridae | Human\|vertebrates | 0 | 0 | 0 | 172 | 0 | 0 |
| Human Immunodeficiency virus | Lentivirus | Retroviridae | Human\|vertebrates | 0 | 0 | 0 | 1 | 0 | 0 |
| Human Immunodeficiency virus | Lentivirus | Retroviridae | Human\|vertebrates | 0 | 0 | 0 | 3,895 | 0 | 0 |
| Simian-Human Immunodeficiency virus | Lentivirus | Retroviridae | Human\|vertebrates | 0 | 0 | 0 | 57 | 0 | 0 |
| Gammapapillomavirus 1 | Gammapapillomavirus | Papillomaviridae | Vertebrates | 14 | 0 | 0 | 0 | 0 | 0 |
| Gammapapillomavirus 10 | Gammapapillomavirus | Papillomaviridae | vertebrates | 0 | 12 | 0 | 60 | 0 | 0 |

*Viruses assigned to bacterial, plant, insect, parasitic, or fungal hosts are not shown
Abbreviations: NTC, no template control; PC, positive control; CSF, cerebrospinal fluid; mNGS, metagenomics next generation sequencing

FIG. 13

```
SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1

gccttggatc tgagccgtt                                                    19


<210> SEQ ID NO 2
<211> LENGTH: 17
<212> TYPE: DNA
<213> ORGANISM: Artificial Sequence
<220> FEATURE:
<223> OTHER INFORMATION: Synthetic primer

<400> SEQUENCE: 2

ggcctaccgc tgcgaat                                                      17
```

PATHOGEN DETECTION USING NEXT GENERATION SEQUENCING

CROSS-REFERENCES TO RELATED APPLICATIONS

The present application is a continuation of U.S. patent application Ser. No. 15/917,286, filed Mar. 9, 2018, which is a continuation of International Patent Application No. PCT/US2016/052912 filed Sep. 21, 2016, which claims the benefit of and priority to U.S. Provisional Application No. 62/221,574, filed Sep. 21, 2015, the entire contents of which are herein incorporated by reference in their entirety for all purposes.

STATEMENT REGARDING FEDERALLY SPONSORED RESEARCH

This invention was made with government support under grant no. HL105704 awarded by the National Institutes of Health. The government has certain rights in the invention.

SEQUENCE LISTING INCORPORATION BY REFERENCE

The Sequence Listing written in file Sequence-Listing_ST25.txt created on May 12, 2020, is 784 bytes, machine format IBM-PC, MS-Windows operating system, in accordance with 37 C.F.R. §§ 1.821-1.825, is hereby incorporated by reference in its entirety for all purposes.

BACKGROUND

Infectious diseases affect the lives and health of millions of patients annually. Failure to obtain a laboratory-confirmed diagnosis for many acute infectious diseases directly contributes to poor patient outcomes and a high cost burden to the health care system. Key areas of unmet clinical need include neurological infections (encephalitis and meningitis), pulmonary infections (e.g., pneumonia), blood infections, and sepsis.

Traditional diagnostic methods, including culture, antigen detection, and nucleic acid amplification, are limited in scope in cases for which there is little clue regarding the identity of the causative agent. DNA sequencing is the process of determining the precise order of nucleotides within a DNA molecule. It includes any method or technology that is used to determine the order of the four bases—adenine, guanine, cytosine, and thymine—in a strand of DNA. DNA sequencing can be helpful in identifying potential causes of disease in patients. For example, alignment processes may be used to identify matching portions of a sample sequence with a reference database of classified reference sequences.

However, DNA sequencing of a sample and the alignment of such sequences for identification of a potential source of disease, typically includes long processing times due to the large amount of information to compare and process in order to identify a matching sample sequence and reference sequence. Additionally, because of the vast amount of data within sequencing data, sequence alignment results can return large numbers of false positives where portions of sequence reads may appear to match to portions of a reference genome that is not in fact present in the biological sample. As such, many alignment results from a DNA sequence alignment process may not be accurate and raw results of such alignments are not useful as-is in a clinical environment because an expert and/or clinician must analyze the results and manually interpret the returned alignment results to interpret the results of the sequencing reads.

Thus, challenges in the field include developing accurate pipelines (or processes) that can quickly analyze millions of reads that include millions of data points that come out of a DNA sequence system, as well as interpret the data so that it is clinically useful to laboratory scientists and/or a physician. Accordingly, there is a need for systems that are capable of quickly and efficiently identifying and interpreting next generation sequencing data for detection of potential causes of disease and/or any other potential applications of DNA sequence alignment information.

Embodiments of the present invention solve these and other problems individually and collectively.

BRIEF SUMMARY

Embodiments are directed to systems and methods for pathogen detection using next-generation sequencing (NGS) analysis of a sample. Embodiments may apply alignment algorithms (e.g., SNAP and/or RAPSearch alignment algorithms) to align individual sequence reads from a sample in a next-generation sequencing (NGS) dataset against reference genome entries in a classified reference genome database. Various embodiments can filter, classify, and display results to a clinician to identify a pathogen or other genetic material in a sample that is being tested. Embodiments can provide various systems that are configured to filter the results of a sequencing alignment and classify a sample quickly and accurately.

As an example, two alignment techniques (one being faster than the other) can be used together to speed up alignment, without sacrificing accuracy. An initial alignment technique can identify which reference genomes in a database match to which sequence reads. For a matching reference genome, an optimally-aligning sequence read can be identified. For the optimally-aligning sequence read, a different alignment technique can be applied, and it can be determined whether any of the new alignment scores to other reference genomes exceed the optimal alignment score for the matching reference genome. If an new alignment score exceeds the optimal alignment score for the optimally-aligning sequence read, the matching reference genome can be removed from a set of matching reference genomes. The set of matching reference genomes can then be output.

As another example, sequence reads can be assigned to a particular classification level, so as to provide accuracy identified of a particular pathogen. Sequence reads can be identified that match to two or more matching reference genomes of the classified reference genomes with at least the minimum alignment threshold. For such a sequence read, a taxonomy identifier can be assigned from classification information to each of the two or more of the classified reference genomes. The taxonomy identifier can include at least two levels of classification. The assigned taxonomy identifier of each of the two or more classified reference genomes can be compared at each of the at least two levels of classification, with levels that do not match being removed. The lowest level shared between the two or more reference genomes can be assigned to the sequence read. Updated alignment results can be provided and include a number of corresponding sequence reads for each of the plurality of taxonomy identifiers.

As another example, background contaminants can be identified and removed from a set of potential (candidate) pathogens that are clinically-relevant. A negative control sample can be used to identify sequence reads from potential contaminating organisms. A ratio can be taken of a first amount of sequence reads from a test sample that align to a matching genome and a second amount of sequence reads from the negative control sample that align to the matching genome. The ratio can be compared to a threshold to identify a set of one or more matching reference genomes have the ratio exceed the threshold. An output can identify a set of one or more matching reference genomes as potential pathogens in the test sample.

Other embodiments are directed to systems and computer readable media associated with methods described herein.

A better understanding of the nature and advantages of the present invention may be gained with reference to the following detailed description and the accompanying drawings. Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers can indicate identical or functionally similar elements.

BRIEF DESCRIPTION OF THE DRAWINGS

FIG. 6 shows an exemplary table including a summary of the results of an exemplary sequencing process for three different sample sequence reads according to embodiments of the present invention.

FIG. 7 shows an exemplary result table including matching reference genomes to three different sample sequence reads as a result of an exemplary sequencing process without filtering or taxonomic classification processes being applied to the results according to embodiments of the present invention.

FIG. 8 shows an exemplary result table including matching reference genomes to three different sample sequence reads as a result of an exemplary sequencing process with a filtering process being applied to the results but no taxonomic classification process being applied to the results according to embodiments of the present invention.

FIG. 9 shows an exemplary result table including matching reference genomes to three different sample sequence reads as a result of an exemplary sequencing process with a taxonomic classification process being applied to the results but no filtering process being applied to the results according to embodiments of the present invention.

FIG. 10 shows an exemplary result table including matching reference genomes to three different sample sequence reads as a result of an exemplary sequencing process with both a filtering process and a taxonomic classification process being applied to the results according to embodiments of the present invention.

FIG. 12 shows table of sequencing statistics according to embodiments of the present invention.

FIG. 13 shows a table of the number of reads from DNA libraries and RNA libraries aligning to viral sequences according to embodiments of the present invention.

Figure 1:
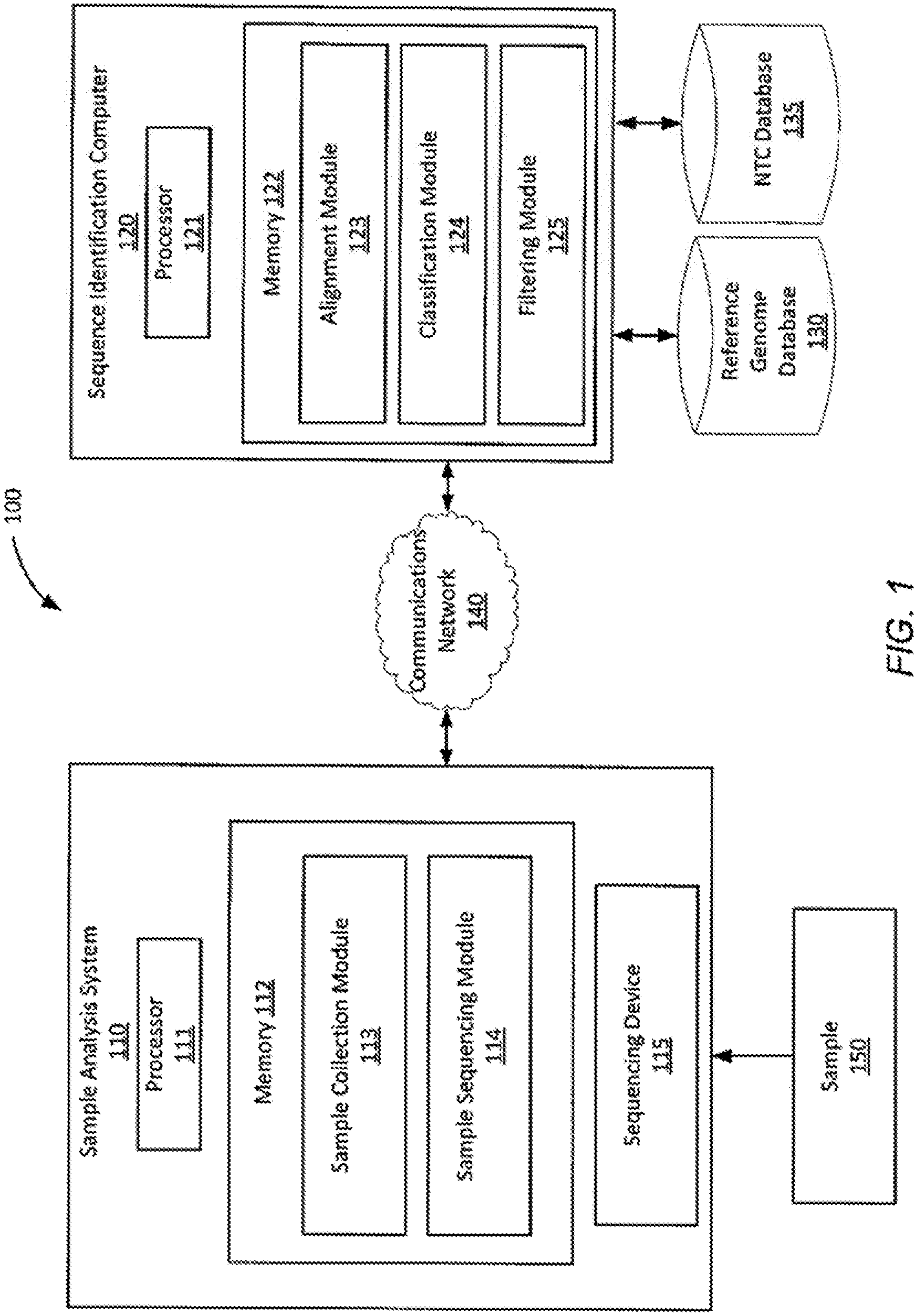
FIG. 1 shows a block diagram of a system 100 for sample analysis, identification, and classification according to embodiments of the present invention.

An Appendix includes Supplementary Tables 1-4.

DETAILED DESCRIPTION

Embodiments can provide processes for rapid analysis of next generation sequencing (NGS) data for pathogen detection. For example, embodiments may be used in a broad, comprehensive pathogen diagnostic for infectious diseases by analyzing sequencing results against many reference genomes, as a metagenomics analysis. The use of unbiased metagenomic next-generation sequencing (mNGS) can provide for detection of all potential pathogens in a single assay. An advantage is the ability to detect all viruses, bacteria, fungi, and parasites in a single, standardized universal test directly from diverse clinical sample types such as cerebrospinal fluid (CSF), bronchoalveolar lavage (BAL), and plasma, thereby maximizing the potential impact on patients with acute, life-threatening infections by early and more accurate diagnosis.

Embodiments may apply alignment algorithms (e.g., SNAP and/or RAPSearch alignment algorithms) to align individual sequence reads from a sample in a next-generation sequencing (NGS) dataset against reference genome entries in a classified reference genome database. For example, as a result of sequencing of a sample, the system may obtain a list of results of reference sequences that align with the sequencing reads of a sample. Individual sequences in the reference genome database (also referred to as a GenBank) are referred to as reference genome sequences and may be identified by genome identifiers (GI). The genome identifiers include reference identifiers used to identify reference sequence genomes stored in the GenBank database. A best GI match can be assigned to each read, and the taxonomy assigned to each GI according to the classified reference genome in the GenBank can be assigned to each read.

Such unbiased analysis (e.g., using the large number of reference genomes in the GenBank) can make accurate detection of specific pathogens difficult as many human samples include flora or background colonization organisms. For instance, a nasal swab has a lot of bacteria in it because that's going to be bacteria that sort of colonize your respiratory tract. Thus, when the system makes a detection, it is difficult to know whether the system has detected a pathogen or a colonizer. Further, because the analysis does not bias or target any individual pathogen, the system could be detecting, for instance, a bacterial contamination of enzyme preps that are used in making the sequencing libraries. So effectively the system may identify laboratory reagent contamination instead of matching to a particular infectious disease.

Accordingly, while the sequencing analysis and matching is sensitive, the analysis may return false-positive matches (e.g., a human read will align to a viral GI due to database misannotations). And, reference genome databases may include many GI entries that are poorly annotated (e.g., “uncultured eukaryote” instead of a particular identification) or, even worse, incorrectly annotated (e.g., [www].ncbi.nlm.nih.gov/nuccore/KC506764.1, annotated as GBV-B when this is actually GBV-C virus). These databases typically allow anyone to add reference genomes and there is no standard for annotating samples.

Further, many of the alignments are not accurate and raw results alone are not useful as-is clinically because an expert and/or clinician must analyze the results and manually interpret the returned alignment results to interpret the results of the sequencing reads. Typically, such interpretation required an expert genomicist or bioinformaticist or someone who is well-experienced with infectious diseases or laboratory medicine and who also understands the bioinformatics. Accordingly, such raw results are not helpful or usable in a clinical laboratory where such processes can provide great value to clinicians caring for patients.

To address this issue (non-specific identification), embodiments can filter and classify sequencing reads to obtain more accurate results and avoid false-positives, maximizing the specificity of detection. Embodiments can filter, classify, and display results to a clinician that can then quickly and easily obtain the results of the sequencing to identify a pathogen or other material that is being tested. Filtering can be helpful because the genome databases may be rife with misannotations and false positive matches.

Further, typical sequencing methods compare sequences to reference databases and then identifying hits based on what the sequence is aligned to. However, the actual interpretation of those hits is more subtle because an expert actually has to analyze the data to determine if some hits are not accurate and/or do not provide enough information to be classified as a particular pathogen. Embodiments can improve the classification of reads by applying a rapid taxonomic classification algorithm to alignment results to provide more accurate and clinically useful results. Additionally, embodiments can annotate the data within the genome reference database so that the system knows what reference genomes are a pathogen, a colonizer, what is considered likely contamination, etc. Embodiments can also provide a user-friendly visualization interface that can be used by clinicians to quickly and easily identify pathogens and other results.

Embodiments can provide a number of advantages including limiting the manual annotation and interpretation of sequencing analysis results to allow quick, efficient, and useful clinical and public health surveillance. For example, embodiments may be used where a patient is sick and a clinician may take one or more samples from the patient to determine what pathogens are present in the samples. The clinician may desire to know whether the patient has a viral infection, a bacterial infection, a fungal infection, a parasite, etc. Any type of biological sample that obtains DNA material could be used to identify potential causes of the disease. For instance, blood, cerebrospinal fluid, respiratory secretion, tissue, stool, etc., may be used to obtain a sequence read of the samples. Additionally, embodiments may be used in blood bank testing, food and water quality testing, environmental testing, animal testing, animal health, or any other area that may be assisted by quickly and efficiently determining potential sequence matches within a sample. However, a sample will likely include a mixture of multiple organisms. Some of these organisms may be from a person, viral, bacterial, and many samples are mostly mixtures of different organisms.

The mNGS assay has been clinically validated for diagnosis of encephalitis and meningitis in cerebrospinal fluid. The assay can incorporate: (1) the analytic wet bench process including handling of patient samples, nucleic acid extraction, mNGS library preparation, and sequence generation on an Illumina HiSeq instrument, and (2) bioinformatics analysis of sequence data and clinical interpretation by trained microbiologists/pathologists. Results of diagnostic mNGS testing from cerebrospinal fluid are reportable in the medical chart and can be used for clinical management. The clinical implementation of the mNGS assay has a direct, positive impact on patient outcomes by increasing the number and proportion of patients with an accurate, clinically actionable infectious disease diagnosis that allows for timely management and treatment. The assay is also able to detect rare, unexpected, or slow growing or uncultivable microorganisms, for which diagnosis is often delayed or missed. The mNGS assay may have particular utility in identifying culture-negative pathogens due to prior treatment with antibiotics. The mNGS assay may also be useful as a “rule-out” test for infectious diseases, which may impact management by increasing clinical confidence in working up and treating non-infectious causes of encephalitis/meningitis such as autoimmune disease with steroids and/or immunosuppressive medications.

The mNGS data can also yield additional information besides whether or not a given microorganism or microorganism type is present or absence. The number and proportion of reads, typically expressed as a “reads per million (RPM)” metric normalized to a negative “no-template” control sample run in parallel, can provide some degree of quantitative or at least semi-quantitative information. In some cases, the pathogen genome coverage may be sufficient to facilitate (1) precise genotyping or strain identification, (2) analysis of single-nucleotide polymorphisms or mutations, (3) the generation of predicted antibiotic/antiviral resistance profiles.

I. Example Systems

Once a clinical sample has been obtained (e.g., from a patient or from an environmental samples, such as a water sample), the sample may be sequenced, and the sequencing results can be analyzed. Various systems and processes can be used. For example, nucleic acid extraction can be performed. A cDNA/DNA library preparation may include adding adapters, although other preparation for other types of sequencing may be performed, e.g., for nanopore sequencing or other single molecule sequencing. The library of templates can be fed into a sequencing device to provide sequencing information, e.g., base calls or raw signals that are used to determine base calls, thereby obtaining sequence reads. The analysis of the sequence reads can include host subtraction; adapter, quality, and low-complexity trimming; and alignment against reference databases such as NCBI (National Center for Biotechnology Information) GenBank.

FIG. 1 shows a block diagram of a system 100 for sample analysis, identification, and classification according to embodiments of the present invention. As shown, system 100 includes a sample analysis system 110 and a sequence identification computer 120. Sample analysis system 110 may be communicatively connected to the sequence identification computer 120 through a communications network 140, which may be any suitable communications network for communicating data. As another example, data may be communicated via a removable storage device, such as a USB drive.

The sample analysis system 110 may be configured to receive a sample 150 (e.g., after library preparation) from a clinician or other operator, sequence the sample to obtain a plurality of sequence reads of genetic material for the sample, and submit the plurality of sequence reads to sequence identification computer 120. A sequencing device 115 can correspond to any sequencing device, such as those produced by Illumina, Pacific Biosciences, or Oxford Nanopore. A processor 111 (e.g., a CPU) can control aspects of sequencing device 115, such as one or more cameras for taking images of the nucleic acids or electrical components, both receiving sequencing signals corresponding to nucleotides of the nucleic acids being sequenced.

A memory 112 (e.g., flash memory, hard drive, DRAM, cache, etc.) can store software for controlling processor 111, which can control sequencing device 115. In some embodiments, a sample collection module 113 can control robotic processes for obtaining a sample (e.g., via a syringe connected to a robotic arm), and perform any automated preparation processes. A sample sequencing module 114 can instruct processor 111 to perform the sequencing, using sequencing device 115. Sample analysis system 110 can perform analysis of the raw sequencing signals (e.g., fluorescent or electrical signals) to identify basecalls of sequence reads, or send such raw sequencing signals to sequence identification computer 120.

Sequence identification computer 120 can process, align, and identify genetic material that is present in the sequence reads to identify pathogens and/or other genetic material that is present in the sample. An alignment module 123 in memory 122 can instruct processor 121 to align the sequence reads to a plurality of reference genomes, e.g., as stored in reference genome database 130. One or more alignment techniques (e.g., a local aligner, such as SNAP) can be used to obtain alignment results, e.g., initial alignments results, as well as subsequent alignment results. A classification module 124 can classify the alignment results to include an accurate taxonomic classification level. A filtering module can filter the alignment results to remove false positives. Sequence identification computer 120 can return results for identifying pathogens and/or other genetic material present in the sample.

Reference genome database 130 can contains a plurality of reference genomic sequences that have been identified and classified as being associated with a particular biological organism. For example, reference sequences of different viruses, bacteria, fungi, human, animal, and/or any other reference DNA sequences of any other biological material may be stored in the classified reference genome database. Sequence identification computer 120 may apply one or more alignment techniques to align the received sequence reads from the sample to the classified reference genome sequences stored within reference genome database 130.

Although FIG. 1 shows the modules and describes the functionality of the modules as being completed by the two systems, in some embodiments, all or a portion of the functionality may be split differently and/or could be completed by a single device. For example, in some embodiments, sample analysis system 110 of FIG. 1 may be coupled to a reference genome database and/or the reference genome database may be stored as part of sample analysis system 110, and sample analysis system 110 may complete all of the functionality described herein.

System 100 can be used to identify and detect pathogens in clinical samples, e.g., for the purposes of surveillance, such as epidemiologic surveillance. For example, it may be desired to look at cases of sequences generated from patients with acute diarrheal illness or fever to identify and detect pathogens. Surveillance can also be performed to detect novel pathogens, thereby allowing pathogen discovery, e.g., when no match is found in reference genome database 130. Another application is use as a diagnostic tool, e.g., by identifying a known pathogen for which treatment is known.

Metagenomic sequencing can include alignment to multiple reference genomes, as may be stored in reference genome database 130. One example of such a database is GenBank, which has more than 20 gigabases in size. With such a large size, the alignment of aligning millions of sequence reads can provide many hits (matching alignments) to different genomes, which is why classification and/or filtering can be useful. There may actually be a pathogen in that sample that is identified by a hit, but there can be false hits, as may occur due to problems in the databases. Databases themselves are not well curated, and there are incorrect or errors in how they are constructed. For example, there may be sequences annotated as hepatitis C virus but may actually be a human sequence for instance and vice versa. The database itself can be cleaned up, as well, e.g., when misannotations are identified, as may be done using BLAST.

Additionally, a sample can include a large amount of background nucleic acids. Techniques can be used to filter out such background sequences, as may be done with a no template control (NTC) sample. NTC database 135 (also called a contaminant database) can store background sequences that have been identified in recent samples, e.g., samples within the last month. Levels (e.g., number of reads) that a background sequence has been quantified can be stored, as is described below.

For the taxonomic classification, individual sequences can be classified according to where they fit on the taxonomic level. For instance, if you have sequences that are aligned to certain regions (e.g., viral or bacterial genome) those individual reads may not be specific for that species. That is, it may not be specific to that viral genome of a viral species. In such a case, the read can be classified using a least common ancestor algorithm to the next higher taxonomic level. Once the sequence reads are classified, the system can then point out what species are specific to the sample, thereby allowing a good prediction that an actual viral species is in the sample.

In some embodiments, the classification can use the results of an initial alignment technique, e.g., SNAP, thereby allowing the classification to start while alignment is being performed for other sequence reads. The efficient alignment can relatively concurrent classification can allow a taxonomic classification in one to two hours. Accordingly, if the alignment results provide 100 hits, the classification can narrow to about 10 to 15. However, for clinical purposes, it is desirable to have only a few hits, e.g., two. The 10-15 hits may be real, but may not be clinically significant. For example, the hits may include microorganisms that are part of the laboratory background contaminants or part of the skin background as part of drawing blood. Techniques to filter out such contaminants are described in more detail below, as well as alignment and classification techniques.

II. Data Analysis

Once the system has obtained the raw sequence reads from the sequencing module, the raw sequence reads are analyzed to obtain an identification of matching reference sequences from one or more classified reference genome databases. Embodiments can provide data with respect to what sequences from different microbial pathogens are detected.

A. Example Pipeline

Figure 2:
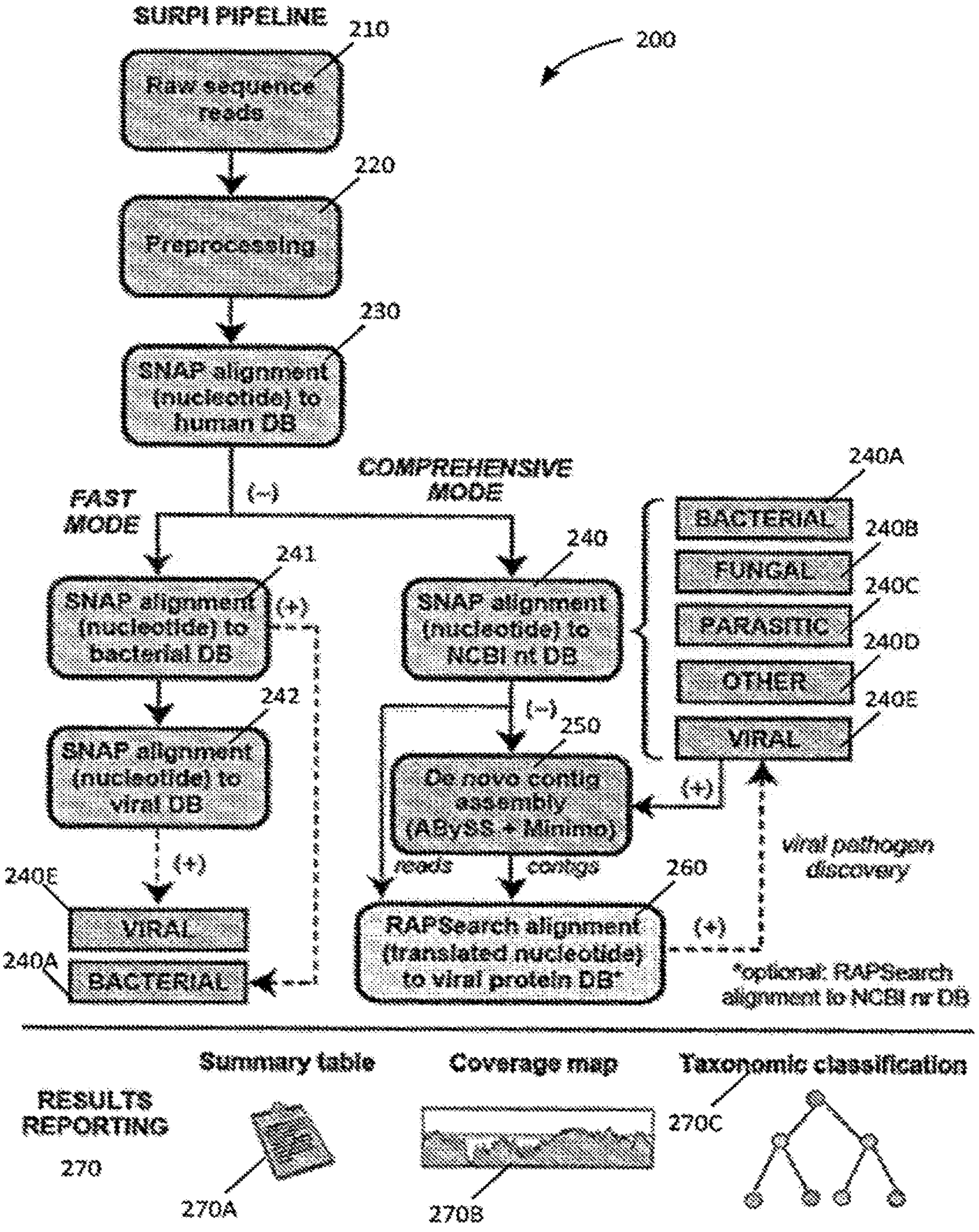
FIG. 2 shows an exemplary method of analyzing and matching sequence reads of a sample to one or more classified reference genome databases according to embodiments of the present invention.

FIG. 2 shows an exemplary analysis process 200 for processing the sequence reads, identifying matching reference genome sequences, and determining matching viral and bacterial matches for the sample sequence reads. Process 200 may be performed with any suitable computer system that is connected to a sequencing machine, e.g., via a network or a removable storage device, such as a USB drive.

At step 210, the raw sequence reads arc received from the sequencing module. The sequencing process may return a large number (e.g., 1, 2, 3, 5, 10, 20, 50, or 100 million reads, or more) of DNA sequence reads from a sample. As examples, the raw sequence reads may be received in fasta, fastq, sam, or bam files. The sequence reads can be obtained in various ways, e.g., from a sequencing of nucleic acids or probe-based methods, such as hybridization arrays. The use of random sequencing that essentially sequences all nucleic acids can be preferable so that a significant number of pathogens (e.g., as many as reference genomes are available) can be detected.

At step 220, the raw sequence reads are preprocessed to trim the reads to remove low quality sequences, remove low complexity sequences (e.g., as would not be very informative), remove adaptors that can be retained at the ends, etc. Thus, the reads may be cleaned-up to ensure that the remaining reads are of high quality. If adaptors are used, the adaptors (adapters) may be ligated to the end of the nucleic acids and used as primers for sequencing, and thus may not relate to the actual nucleic acids. The low complexity reads (e.g., with many repeats) can be difficult to align, and thus removed. The quality of a read can be determined based on the quality of the basecalls, which may be determined based on the sequencing signals.

At step 230, an alignment module (e.g., alignment module 123) performs a sequence alignment analysis for the sample sequence reads to the reference genomes. In some embodiments, the alignment analysis may be performed in reference to a host genome database first and any sample sequence reads that align to the host may be removed from the sequence. For example, in embodiments that are identifying pathogens associated with a human sample, the sequence reads may be aligned with a reference human genome database and any matches may be removed (since no pathogens should be present in the human reference genome database). Comparison can be made to multiple reference human genomes.

Thus, embodiments can use computational subtraction to speed up the identification processes to remove any sequence reads that align with the host (and thus are not helpful for identifying biological material from other entities (i.e., pathogens)). In embodiments where a single large reference database is used, any results that are identified as matching with a human reference genome could be removed. However, by applying the full 100% of the sequence reads and not subtracting them before aligning with the full reference database, the process may be slower than if those sequence reads were removed before comparing to the large database of reference genomes.

The host database (e.g., human genome database) may include fewer genomes than the entire reference genome database. Accordingly, sequencing can be faster than comparing to all possible reference genomes. Thus, for relatively high quality sterile samples, applying such a host filtering method may remove most of the background reads quickly. For example, for a good sample, the removal of the host matches could take the analysis from potentially 100% of the reads down to maybe less than 10% of the reads. Thus, 90% of the sample sequence reads can be removed by alignment to a host (e.g., human) database.

Additionally, in some embodiments, a host database could include similarly related genomes that are not specifically from the host. For example, for the human example provided above, the system could also include primates that have similar genomic references to humans. This provides a more comprehensive host analysis and provides even faster and more effective subtraction of host matches.

Next, depending on the mode of the identification process, either a comprehensive mode or a fast mode can be performed to identify one or more matching reference genomes associated with the sample sequence reads. The fast analysis may only align the sample reads to a reference genome database of bacterial and viral reference genomes. Thus, the fast mode analysis may not identify all potential genomic matches in the sample sequence reads but will focus on the analysis on potential bacterial and viral matches due to the focus of the process on identifying pathogens within the samples. The comprehensive mode may align the sample reads to an entire nucleotide classified reference genome database that includes reference genomes from bacterial 240A, fungal 240B, parasitic 240C, viral 240D, and other 240E reference genomes.

At step 240 of the comprehensive mode, the alignment module performs a sequence alignment analysis for the sample sequence reads to the reference genome database, e.g., to reference genomes 240A-240E, Steps 241 and 242 of the fast mode may only perform alignment to the bacterial database 240A and viral database 240E, respectively. Any number of different sequencing algorithms may be used in embodiments of the present invention. For example, the "Scalable Nucleotide Alignment Program (SNAP)" algorithm includes a nucleotide aligner that takes raw sequence data and aligns it to nucleotide reference databases. SNAP is extremely fast and by using fast sequencing algorithms, the analysis processes of the present invention may return results extremely fast. While other analysis methods (i.e., "pipelines") may analyze a sample sequence data within days, weeks, or months, embodiments of the present invention can analyze the sample sequence data in minutes to hours. Fast sequencing analysis is critical in a number of applications including, for example, infectious diseases analysis that can be paired with a next generation sequencing essay that can diagnose infectious diseases and get results to physicians regarding patient care within 8-12 hours, or as soon as possible For example, in some embodiments, the system may align the sequence reads from the sample to all classified reference genomes in GenBank using a SNAP alignment algorithm. However, the GenBank is growing very fast (e.g., doubling every year) so it can be important to limit the number of reads being analyzed to improve the speed of the alignment analysis with the reference database (e.g., GenBank). For example, in some embodiments, a specific subset of the GenBank may be used to improve analysis speeds further. For example, if the clinician is not concerned about potential plant matches, such reference genomes may not be applied to the alignment analysis and/or a separate subset or different database may be used to avoid potential plant genetic matches. Accordingly, some embodiments may align to a tailored search for potential pathogens, bacteria, etc. and avoid aligning to reference sequences that are not a part of the tailored search.

At step 250, in the comprehensive mode, de novo contig assembly may be performed to obtain contigs associated with the results of the assignment from the classified reference genome database. Example assembly software include ABySS and Minimo.

At step 260, in the comprehensive mode, the reads and the contigs are used to align the translated nucleotides using another alignment algorithm (e.g., RAPSearch) and compared to a viral protein reference database. To generate translated nucleotides, the sequencing reals are translated in all 6 reading frames and the resulting amino acid sequences are then compared to a protein reference database. The output of RAPsearch is similar to that of BLAST but lists alignments that exceed a predesignated E-value significance threshold.

At step 270, the results of the alignment algorithms are obtained, and may include a summary table 270A that provides the matching viral, bacterial, fungal, parasitic, and other reference genomes that have aligned to the sample sequence reads. Thus, in response to the alignment, the system can provide a table that shows alignments to bacterial and viral reference genomes. Summary table 270A may list all the hits to the different species in the sample and the different genera in the different families of organisms found in the sample, e.g., according to taxonomic classification 270C. For example, the system may divide the results into viruses, bacteria, non-cordate eukaryotes (basically fungi and parasites that do not have a backbone), human, as well as an "other" category. Cordates are all higher level eukaryotes, eukaryotic organisms that have a backbone. Eukaryotic organisms that do not have a backbone are more often microorganisms. These categories are used in order for the system to identify fungi and parasites as well as other microorganisms that do not have backbone (e.g., invertebrates like worms). The system may find matches that are not necessarily microorganisms, for instance, the system may be capable of diagnosing a tape worm infection.

Thus, at the end of the alignment process and in an initial table, the system may provide matches for different bacteria and may include the number hits for each type of bacteria, virus, etc. Furthermore, in some embodiments, de novo assembly may be applied to actually recreate the genome and coverage maps 270B of the genome may be provide to indicate how well the reads cover the genome of one the genomes in the list.

Accordingly, the results of the alignment process of FIG. 2 can provide all possible matches for one or more DNA sequence reads from a sample. For example, summary table 270A may include fifty bacteria and/or twenty viruses. Next the question becomes which one of these or are all of these causing the potential infection? Some of these results may be contaminates, some might be colonizers, etc., so the results must be interpreted to identify a potential candidate as the pathogen that is causing an infection. Traditionally, if a system detects three different bacteria, a clinician has to interpret the matches to determine which one of those three bacteria or which combination of bacteria are the most important in terms of causing the disease. Accordingly, it is important to be able to limit as many potential false-positives and incorrect matches as possible to assist clinicians and users of the system to identify the most likely one or more pathogens responsible for an illness.

Accordingly, embodiments of the present invention provide (1) filtering, (2) taxonomic classification, and (3) best match algorithms for identifying and providing the most useful data to a clinician. Additionally, embodiments provide additional features including RNA sequence removal and on-the-fly annotation of database entries to further assist interpretation of alignment results.

B. Flowchart of Example Data Analysis

Figure 3:
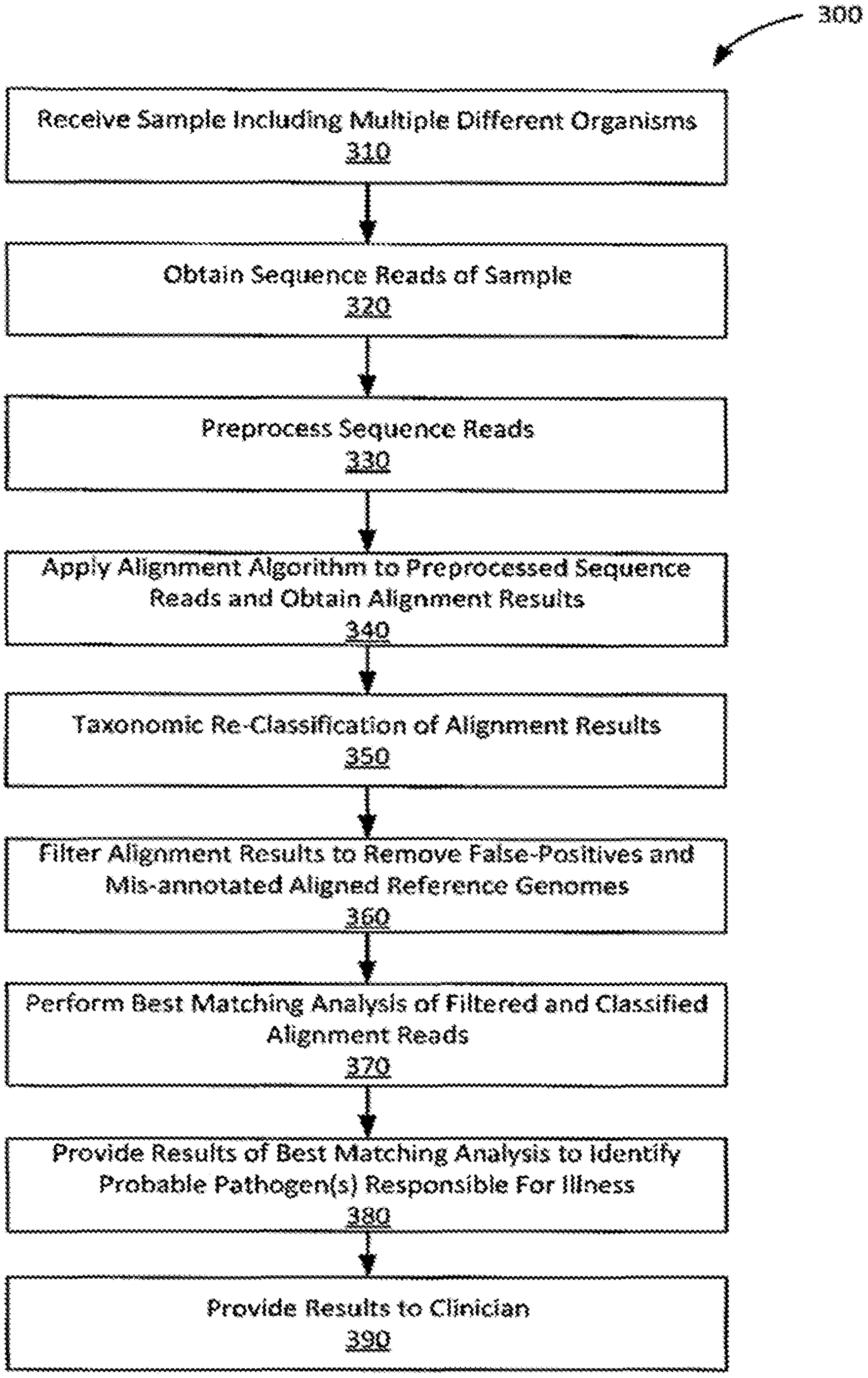
FIG. 3 shows an exemplary method of analyzing and matching sequence reads of a sample to one or more classified reference genome databases and identifying biological material corresponding to sequence reads of the sample according to embodiments of the present invention.

FIG. 3 shows a streamlined process 300 for identify, matching, and interpreting sample sequence read alignments with classified reference genome databases according to embodiments of the present invention. Aspects of process 300 may be performed in a similar manner as process 200. Process 300 may be performed using system 100.

At step 310, a system may receive a sample from a patient and/or other biological item and/or entity. The sample may be provided by a clinician or other operator of the sample analysis system. The sample may form nucleic acids that have already been prepared into a library for sequencing.

At step 320, the system may obtain sequence reads of nucleic acids from the sample. Any suitable method for obtaining DNA sequence reads may be used, e.g., as described herein.

At step 330, the system may preprocess the sequence reads. The preprocessing can include trimming sequence reads and removing some reads, e.g., low quality or low complexity reads.

At step 340, the system may apply an alignment algorithm to the preprocessed sequence reads and obtain alignment results for the sequences reads. Each read can be aligned to a classified reference genome database, e.g., including millions of reference genome sequences. The alignment may return millions of "hits" or alignments to the classified reference genome database.

Some of the matches may not be perfect and may include sequence reads that match a portion of a reference genome sequence. A quality value may be returned with the alignment results that indicates a measurement and/or magnitude of similarity between the sequence read and the reference genome sequence. Additionally, individual reads may align with more than one reference genome. Accordingly, alignment results may include an identifier of the reference genome that was matched, classification information associated with the annotated information provided when a reference genome was uploaded to the classified reference genome database, and a similarity measurement indicating the quality and/or closeness of the alignment between the sequence read and the reference genome.

At step 350, the system may provide a taxonomic reclassification of the alignment results for reads that have aligned to multiple reference genome sequences with different taxonomic classifications. For example, the system may compare levels of classification between multiple aligned reference genomes for a particular sequence read and may remove one or more classification levels that do not match between the reference genome sequences aligned with a particular sequence read. Additional details and steps associated with the rapid taxonomic classification process is provided in reference to FIG. 4 below.

At step 360, the system may filter the alignment results to remove false positives and mis-annotated or mis-classified reference genome sequences that aligned to the sequence reads of the sample. For example, the system may select a best match sequence read for an identified reference genome and may apply a second alignment technique to the best matching sequence read to identify if the same reference genome aligned with the second independent alignment. If the alignment of the sequence read does not match the same reference genome, the read and the reference genome may be removed from the alignment results as the reference genome is likely a false positive hit. Additional details and steps associated with the filtering steps are provided in reference to FIG. 5 below.

In some embodiments, the filtering may include removal of a reference genome as a viable pathogen when the taxonomic classification is listed in the results of a no template control (NTC) for the current experiment or a database of previous NTC results. Further details are provided in a section below.

At step 370, the system can use the updated alignment results including the filtered and taxonomically re-classified sequence reads to identify one or more best matches for the sequence reads from the sample. For example, the best match may be selected based on the reference genome sequence that aligned with the most sequence reads.

At step 380, the system provides the results of the best matching analysis to the analysis system being operated by the clinician. The results may be provided via a network connection. The results may include the most probable one or more pathogens that may be responsible for a patient's illness.

At step 390, the analysis system provides and/or displays the results to the clinician. The results can be provided in any variety of ways, e.g., visually or by audio. The results can indicate a treatment to be provided, thereby providing a therapeutic intervention.

C. Example Best Match (GI Picker)

An objective of embodiments can be to pick the most informative one or more genome identifiers (GI) out of the GIs matched by all the sample reads of a single taxonomic assignment, a particular species. As part of the analysis, a score can be determined for each of the matched reference sequences, specifically each GI. In some implementations, the scores are determined for only GIs at a given taxonomic level, e.g., species. In other implementations, the total scores are determined for GIs across various (e.g., all relevant) taxonomic levels, with a top score being picked across all the GIs. The total scores can be determined from respective scores of various properties.

In some embodiments, each of the matched reference sequences can be scored as to any or all of length, coverage, identity, and percent identity. Thus, four scores can be determined and used to determine a total score. Examples of how the scores can be determined are provided below.

Length is the length of the reference sequence. Thus, a length score is larger for longer reference sequences. Therefore, a species of microorganism that has a larger genome would have a longer length score. In some embodiments, matches can be ranked by whether or not complete versus partial genomes are available in the database, where use of only a partial genome would affect the length score.

For each reference sequence, a coverage score can be determined. In one embodiment, the coverage score can be determined as a cumulative score representing a sum of the counts of aligned reads at each genomic position (e.g., base position) along the reference sequence. In another embodiment, the coverage score can be determined using a sum of genomic positions that have at least one read aligned to that position, e.g., regardless if there is a match that position. The coverage score may be a percent of the genome that is "covered" by at least one aligned read, and thus the sum of genomic positions that have at least one read aligned to that position can be divided by the total number of positions in the database for that reference genome.

For reference sequence, the identity score can be determined as a cumulative score representing a sum of fractional scores at each genomic position. A fractional score can be calculated as the number of aligned reads with a nucleotide matching the reference sequence divided by the number of aligned reads whether or not matching the reference sequences (i.e., the total number of aligned reads covering the position). Thus, a genomic position will have a larger fractional score when there are fewer mismatches of reads at that position.

Percent identity can be calculated by dividing the identity score by the coverage score.

Once the individual scores are determined, an overall score can be calculated for each reference sequence (taxonomic identifier). In one embodiment, the overall score can be determined by adding 'length' and 'identity' and multiplying the sum by 'percent identity'. The reference sequences can be ranked by the overall score, e.g., in descending order. And, a top score(s) can be selected, e.g., by choosing the first reference sequence in the list. In some embodiments, more than one reference sequence can be selected, e.g., all having a total score above a score threshold. In other embodiments, the top N or X % of taxonomic identifiers can be identified.

Accordingly, for each sample, a score can be determined for each relevant GI (e.g., a set of taxonomy identifiers) at one or more taxonomic levels (e.g., for each species, genus, family, etc.). The scores may be determined only at one taxonomic level, or at a given level and all GIs at lower levels. As an example for each GI, the reads aligned to that GI can be grouped. For each GI, the coverage and identity score can be determined in the following manner. For each alignment of a read, the following calculation can be performed for each alignment position: map the read to the genomic position of the GI, the position coverage score is increased, and the position identity score is increased if there is a match. Across all genomic positions for the GI, the total coverage score can be increased by one for each position that has a position coverage score greater than zero. The total identity score can be determined as the sum of the fractional scores, computed as the position identity score divided by the position coverage score. The percent identity score can be determined as the total identity score divided by the total coverage score.

In some embodiments, the following pseudo code can be used:

```
for each sample
  for each species
    group by GI all reads and alignment data
    for each GI
      score covered and identity
        for each alignment
          for each alignment position
            map to GI position
              covs[position] += 1 if
            match/mismatch
              idents[position] +=1 if
            match
        sum across all GI positions
          covered +=1 if covs[position] >0
          identity +=idents[position]/covs[pos
        ition]
      score percent identity = identity/covered
    sort descending by (length + identity)*percent
  identity
    choose first in sorted list
```

D. Mapping Reads to Selected GI

In various embodiments, an output (e.g., a file) can contain the picked reference sequence (GI) and a consensus sequence of the reads mapped to it. The term "coverage" can be used in two contexts: (1) one of the sub-metrics that make up the overall score for picking a GI; and (2) an overall metric, inferred from a coverage map file, for how comprehensively a set of mapped reads cover the picked GI.

For picking a GI, a particular species can have multiple genomic identifiers for different reference sequences in a database. The database of reference sequences used can vary or be constructed from some combination of separate databases. On database is the NCBI 'nt' database. It is highly redundant, and often mis-annotated. A single species can have thousands of entries, or GIs. A GI can be picked using embodiments of the best match algorithm above.

After picking a GI for each species, scores can be determined for each of the selected GIs (e.g., one for each species). The scores can be determined using all reads assigned to the species level, and can include reads assigned to higher levels. The scores can be determined as described above, and scores exceeding a threshold, e.g., an absolute number, a value at which the top N scores are above (where N is an integer), or a value at which the top X % of scores are above.

Assigned reads at the subspecies, species, genus, or family level can also be mapped to the selected GI for visualization. Mapping of reads at higher taxonomic levels (genus or family) will increase the coverage of the GI (the percentage of nucleotides that have at least one read mapped to it), but can also incur a risk of erroneous mapping from different species or genera in the sample. Real-time visualization of the coverage maps and pairwise identity plots can facilitate expert interpretation for clinical results reporting.

III. Rapid Taxonomic Classification

Some embodiments may analyze clinical or environmental metagenomic data (e.g., metadata) to classify the origin of each of the millions of next-generation sequencing reads (e.g. bacterial, viral, human, etc.) that are returned by the alignment results. However, individuals reads may be informative only at a given taxonomic level (species, genus, family, etc.). For instance, a read in the conserved matrix gene of influenza viruses may be identical (or nearly identical) in influenza A and influenza B, and thus this read cannot be used to distinguish between influenza A and B. This is problematic if one is interested in species or strain level identification, which is critically important in infectious disease diagnosis (examples: *Bacillus anthracia*/anthrax versus *Bacillus cereus*; enterovirus versus rhinovirus; Ebola Zaire versus Ebola Reston).

As such, some embodiments may provide a taxonomic classification algorithm that removes some of the hits from consideration through the metagenomic data provided through the classification of the reference genomes. The taxonomic classification algorithm may apply a least common ancestor (LCA) approach where taxonomic identifiers for each of the associated reference genomes are analyzed to identify the lowest level of shared ancestry between two or more reference genomes. For instance, if a sequence has hits to both a human and a virus, and the match is conserved between a human and a virus, then the algorithm would move the result up to the proper taxonomic level, which would in this case be above the kingdom level. In such embodiments, the system would assume that it mapped to the human and would remove the result since the taxonomic classification moved up to the kingdom level.

As another example, if the system returned hits for a single virus but different versions of the virus (e.g., influenza A and influenza B), and the hits are indistinguishable between influenza A and influenza B, then those sequences would be assigned to the influenza genus, and not to the species level (i.e., Influenza A and B). Thus, the system would move the classification for this reference genome up to a higher level (e.g., family enterovirus instead of mapping to two different enterovirus species—influenza A and influenza B).

Such classification allows a clinician to look at the results at different levels and provide potential options for treatment. Using the influenza A or influenza B example above, the result may indicate that the system matched either influenza A or influenza B instead of influenza A. For example, if the system is analyzing an influenza A sample (i.e., a sample taken from a patient infected with influenza A), the sequence results will likely return that 90% of the sample sequencing reads are going to align influenza A and 10% are going to align to influenza B because of the indistinguishable portions of the genetic material between influenza A and B. Reads may be from regions that are highly conserved between these two species of influenza. Thus, a clinician may not know, looking at the raw data, whether this patient is infected with both influenza A and B, is infected with influenza A alone and it just happens to be that B was misaligned to influenza B, or vice-versa. However, by applying the taxonomic classifier and by properly classifying those reads that were initially assigned to influenza B, the system moves up the classification to the genus level, and the remaining reads assigned to influenza A would allow a clinician to make a determination that the patient has an influenza A infection instead of the erroneous call, which would be this a dual infection with influenza A and B.

Thus, after shared reference genomes have been classified at the appropriate level, the remaining reads in the alignment results should be specific at each taxonomic level and thus, the remaining hits that are species-specific are known to be particular to that species. By removing the alignment results that are shared between multiple reference genomes sharing a genus, family, etc., the results will be more accurate and usable by the clinician. The reads that remain after shared reference genomes of the same genus have been reassigned to a genus as opposed to a particular species associated with the aligned reference genome. Identifying species-specific reads can be extremely informative to clinicians where the clinicians know that the read is specific to the particular species, sub-species, strains, etc. It can also be useful to know the higher taxonomic level information including the number of reads at a particular genus, family, etc. Thus, embodiments provide more informative and accurate information for a clinician.

A. Classification Method

Figure 4:
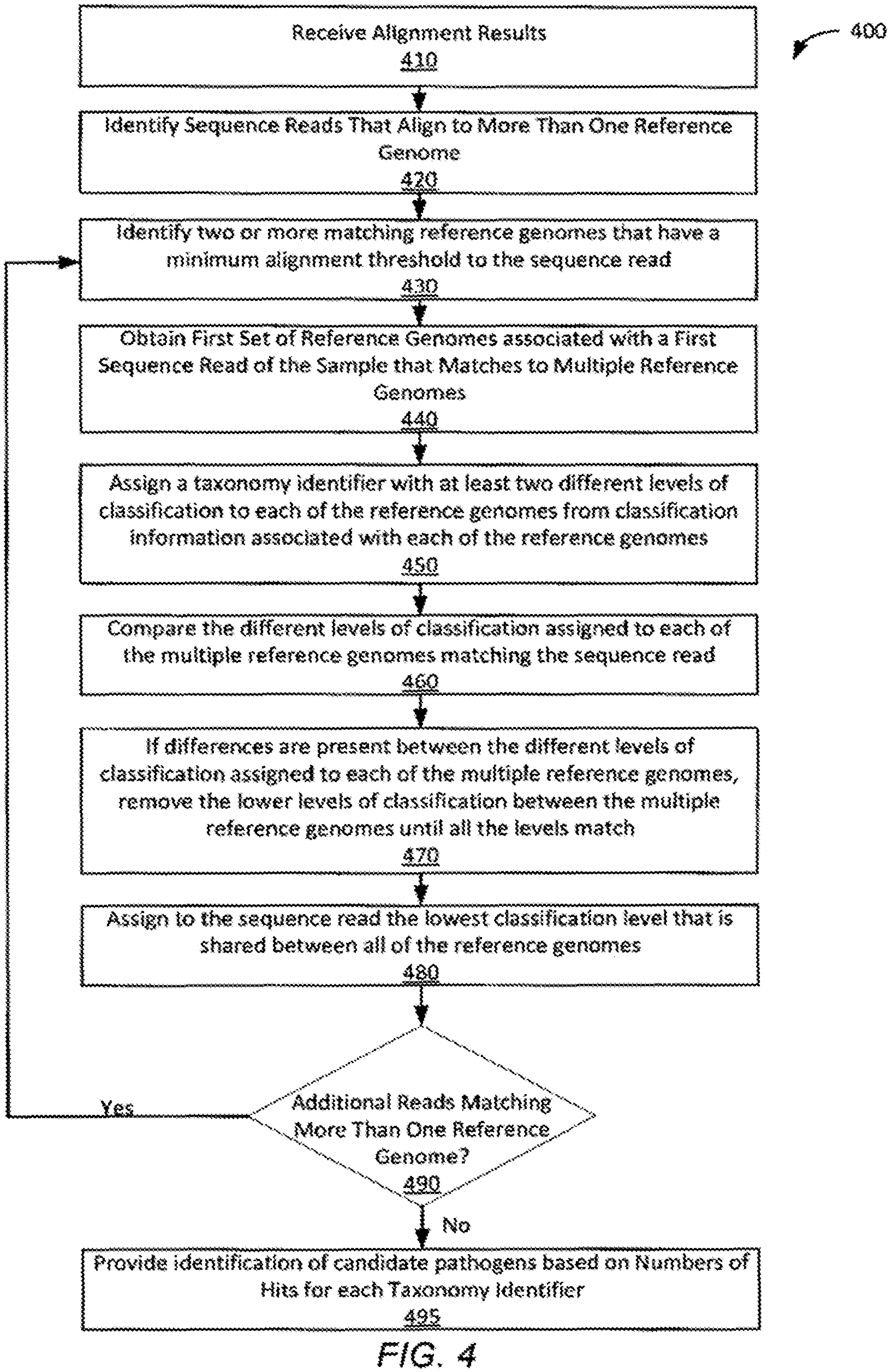
FIG. 4 shows an exemplary method of applying a taxonomic classification algorithm to the results of an alignment process to one or more classified reference genome databases for sequence reads of a sample according to embodiments of the present invention.

FIG. 4 shows an exemplary process 400 of taxonomic classification for find the appropriate taxonomic classification level for reads and aligned reference genomes that may share portions of genomic sequences between various species, genus, family, subspecies, strain, lineage, etc. Thus, embodiments allow for appropriate identification of possible reads aligned to a reference genome to allow the system to provide the best possible identification of potential pathogens causing illness and/or present in a sample from a host organism. Process 400 may be performed by system 100.

At step 410, the system receives the alignment results from applying an alignment algorithm to the sequence reads from the sample. In some embodiments, the alignment results may have been previously filtered using techniques described herein. The rapid taxonomic classification process may be performed concurrently with the alignment process and thus, before the filtering process has been completed. Thus, the system can receive a plurality of sequence reads obtained from a sequencing of DNA molecules from the sample of biological material where the sample includes DNA molecules from a plurality of organisms and aligns the sequence reads using an alignment technique to align the plurality of sequence reads to a plurality of classified reference genomes in a database.

The system may obtain initial alignment results that include, for each of at least a portion of the sequence reads, a matching reference genome to which the sequence read aligns. The initial alignment results may further include classification information for each of the matching reference genomes where the classification information includes a taxonomic identifier including multiple classification levels for each reference genome. For example, a reference genome (e.g., enterovirus D) may include a species (e.g., enterovirus D), germs (e.g., enterovirus), and family (e.g., picornaviridae) classification level within a taxonomic identifier. Many other classification levels may be also be assigned and included in the taxonomic identifier and corresponding classification information with the initial alignment results for each aligned reference genome.

At step 420, the system identifies a set of the sequence reads that aligned to two or more of the classified reference genomes. For example, in FIG. 7, the human rhinovirus and the human enterovirus K1105 both have a single hit. However, as can be seen in results table 900 of FIG. 9, after classifying the initial results, both of these reference genomes have been re-classified. Accordingly, these reference genomes matched with a read that aligned to multiple reference genomes. Step 420 can ensure that sequence reads that align to only one reference genome are not subjected to unnecessary further analysis, as those sequence reads can be classified based on the single matching reference genome.

Steps 430-490 can be performed for each of the sequence reads identified in step 420.

At step 430, the system identifies two or more matching reference genomes of the classified reference genomes to which the sequence read aligns with at least the minimum alignment threshold. For example, using the example provided above in reference to FIG. 7 and assuming that a sequence read matched to both of these reference genomes, the system may select a read that aligned to both of these species-specific reference genomes. The minimum alignment threshold can ensure that a matching reference genome is sufficiently similar to the sequence read at a given location. The minimum alignment threshold may be used for all sequence reads, or can vary for different sequence reads, e.g., based on the specific alignment quality for each of the matching reference genomes or as a result of taking the highest N matching reference genomes (e.g., as determined by an alignment score, such as a number of mismatches).

At step 440, the system selects a set of reference genomes for a sequence read that matches to multiple reference genomes. For example, using the example provided above, the system may select the human rhinovirus and the human enterovirus K1105 reference genomes that may have been associated with the same read. The selected set of matching reference genomes may correspond to those identified in step 430. In other embodiments, other factors may be used to determine the selection of the set of reference genomes to use. Such other factors can include the magnitude of the differences between the "best" and "second-best" alignments, the genomic sequence diversity corresponding to the detected microorganism (e.g. viral genomes are most diverse than bacterial genomes), and the completeness of the available reference databases, including the availability of "near-neighbor reference genomes (i.e. genomes that are closely matched in the reference database).

At step 450, the system assigns a taxonomy identifier from the classification information to each of the two or more of the classified reference genomes. The taxonomy identifier may include at least two levels of classification (e.g., species, genus, family, etc.) and the levels may have a hierarchy such that there is a lower level (e.g., species) and at least one higher level (e.g., genus, family, etc.). For example, using the example of FIG. 7, the system may assign the taxonomic identifier including a species of human rhinovirus species, a genus of enterovirus, and a family of picornaviridae to the first reference genome and a species of human enterovirus K1105_171204, a genus of enterovirus, and a family of picornaviridae to the second reference genome.

At step 460, the system compares the assigned taxonomy identifier of each of the two or more classified reference genomes at each of the at least two levels of classification. For example, using the example of FIG. 7, the system may compare the species, genus, and family of the human rhinovirus sp and the human enterovirus K1105_171204 reference genomes. The system may begin at the lowest level (e.g., species or sub-species level) and compare whether they are the same.

At step 470, the system removes each level of the at least two levels from the assigned taxonomy identifier that do not match between the two or more classified reference genomes. For example, using the using the example of FIG. 7, the system may determine that the sub-species and species between the human rhinovirus sp and the human enterovirus K1105_171204 reference genomes are not same and may remove those levels from the results. Thus, if differences are present between the levels of classification assigned to each of the multiple reference genomes, the lower levels of classification between the multiple reference genomes may be removed until all the levels match.

At step 480, the system may assign to the sequence read the lowest level of the at least two levels of the assigned taxonomy identifiers that is shared between the two or more classified reference genomes. For example, using the example of FIG. 7, the system may determine that the lowest shared level that is shared is the genus level of enterovirus for the human rhinovirus sp and the human enterovirus K1105_171204 reference genomes. Accordingly, the system may assign the lowest level of the taxonomic identifier for the two reference genomes to be the genus level of enterovirus for the two reference genomes. In such a case, the identifier for the genus level would be assigned to the sequence read. If none of the at least two levels of the taxonomy identifier match, an unassigned state may be associated with the sequence read.

As shown in FIG. 9, the species results for both the human rhinovirus sp and the human enterovirus K1105_171204 reference genomes have been removed from the results table, and instead the reads have been combined into a genus match for the enterovirus that has a read of 10,461 sequence read hits. Accordingly, the results indicate that 10,461 sequence reads aligned with reference genomes that were shared between various species within the enterovirus genus, but that were not specific to a particular species. Accordingly, the results are simplified for a clinician.

At step 490, the system determines whether all of the reads matching multiple reference genomes sequences have had taxonomic classification processing applied. If there are additional reads matching multiple reference genomes to be analyzed, the system may repeat the process for the next sequence read in the initial alignment results (and may return to step 430). This process may continue until all of the sequence reads matching to two or more reference genome sequences have been analyzed to ensure the reference genomes have the appropriate level of classification.

At step 495, the system provides an identification of one or more taxonomy identifiers corresponding to one or more candidate pathogens based on numbers of corresponding sequence reads assigned to each of the plurality of taxonomy identifiers. The identification can be the taxonomy identifiers with or without additional information. For example, the number of reads assigned to each of the identifiers may or may not be included. The fact that the identifier(s) are being provided can indicate that the identifier(s) are candidate pathogens, i.e., a sufficiently high likelihood of existing in the sample based on the number of reads assigned. Various criteria can be used to determine whether a pathogen is identified as a candidate pathogen, e.g., using best match algorithm for picking one or more identifiers (as described herein) and criteria for determining whether the best matched taxonomy identifier provides a sufficient match to be identified as a candidate pathogen.

In some embodiments, sequence reads having an assigned taxonomy identifier can be used to identify the one or more taxonomy identifiers corresponding to one or more candidate pathogens. For each of a plurality of taxonomy identifiers, a total score can be determined based on at least coverage of a reference genome corresponding to the taxonomy identifier. The total scores can be ranked, and one or more taxonomy identifiers exceeding a threshold can be identified.

In one embodiment, updated alignment results can be provided to a clinician where the updated alignment results include a number of reads for each of the plurality of taxonomy identifiers. As shown in FIGS. 7, 9, and 10, the effect of taxonomic classification is to properly classify reads to their correct taxonomic level. Two reads (751 and 752 in FIG. 7), one aligning to rhinovirus A 752, and the other aligning to human enterovirus K1105 751, are correctly bumped up to the genus level (genus Enterovirus) in FIG. 9. By doing the taxonomic classification, the interpretation of the data is that there is only one species of enterovirus identified with a large number of sequence read alignments (enterovirus D) in the sample (yellow shading), and not two different species (rhinovirus A and enterovirus D, for example). Table 1000 of FIG. 10 shows a results table 1000 for classification and filtering.

In some embodiments, the classification of a read can begin once alignment results for that read are obtained. Thus, the alignment results for all reads are not required before classification can begin. Accordingly, the two processes may be performed in parallel (e.g., in separate threads) with the output of the alignment thread being used by the classification thread, with the classification thread operating slightly delayed as needing to wait for the alignment results for a first read.

Once the candidate pathogen(s) are identified, additional available clinical and laboratory data can be helpful in determining whether or not the detected organism is pathogenic (i.e. causing disease) in the host organisms (e.g. human patient). The detection of the presence of a potential pathogen in a clinical sample does not necessarily mean that it is causing disease; the potential pathogen could be a colonizer, for instance, or a bystander and have nothing to do with the host organism's illness. If the candidate pathogen is deemed to be pathogenic by clinical and other criteria, the detection can be used to guide clinical interventions, which can include (1) drug therapy (e.g. prescribing or administration of a targeted antimicrobial agent), (2) drug discontinuation (e.g. discontinuing a drug that was administered empirically in the absence of a definitive diagnosis), (3) vaccination, if a vaccine is available and efficacious after infection (e.g. rabies), and (4) medical procedures (e.g. valve replacement in cases of fungal endocarditis, for which antifungal therapy alone is ineffective). The failure to detect a candidate pathogen may also be clinically useful to "rule out" infection as the cause of illness, which can guide clinicians to work up and treat for non-infectious causes (e.g. administering intravenous immunoglobulin and steroids for autoimmune disease).

Accordingly, when the sample of biological material is from a host organism, a clinical intervention can be performed for the host organism based on the identification of the one or more taxonomy identifiers corresponding to the one or more candidate pathogens. The clinical intervention can include the examples above. The intervention can include actually performing/administering any of the above procedures or prescribing them.

B. Minimum Alignment Threshold

The alignment results can provide a distance (e.g., an edit distance) between the sequence read and the matching region of a reference genome. The distance can provide a measure of how many nucleotide differences are there between the actual sequence read and the reference. An edit distance can be the minimum number of editing operations (e.g., insertion, deletion, and substitution) to transform the read into the reference genome, or vice versa. Using the edit distance can help to perform the classification quickly.

Once a distance is obtained, the reference genomes can be ranked by the distance. The taxonomic classification can place the read at different species, genus, or family level based on edit distances to different matching reference genomes. Thus, the taxonomic locations for each of the reference sequences can be determined.

The desired edit distance for determining matched alignments will vary depending on the sequence diversity of the organism. Thus, the minimum alignment threshold can vary depending on which reference genomes are involved. For instance, viruses have more divergent genomes (meaning there is a lot of diversity). For viruses, a relative large threshold can be used, e.g., up to 12 mismatches in the fixed read length. For bacteria and fungi, a smaller distance may be tolerated because bacterial genomes that fit in the same species are highly identical; we want to be able to not only identify the species but we want to be specific.

For instance, if there are two different subtypes of enteroviruses, 70 and 71, there can actually be up to 30% difference by sequence between those two viruses. On the other hand, two bacterial species, such as staph aureus and staph epidermidis, can be 99% identical across the genome. Edit distances can be used as a criteria for classifying these reads, and different taxonomic groups you would require different edit differences. A suitable matching threshold distance can be determined empirically meaning from clinical data or data generated from positive and negative controls where it is known what is in the sample, e.g., what pathogens are in the sample.

IV. Filtering Reference Genome Sequence Hits

One embodiment of the present invention is directed to filtering out sequences that appear to be false positives and/or are incorrectly annotated and/or classified. For example, some reads may initially appear to align to a particular classified reference genome using a first alignment algorithm (e.g., a global alignment algorithm like, for example, SNAP or Needleman & Wunsch) but a more comprehensive alignment (e.g., using a local alignment algorithm like, for example, "Basic Local Alignment Search Tool" (BLASTn) or Smith & Waterman) shows that even a best read can actually align to a different reference sequence using different alignment algorithms.

Furthermore, some reference genomes with a GenBank or other large database of classified reference genomes may be mis-annotated taxonomically (i.e., are classified incorrectly). Additionally, some reference genomes may include portions of sequences that can be assigned to multiple taxonomies. If a sequence in the dataset aligns to the "erroneous" portion of that reference genome sequence, it will be mis-assigned by an alignment process. For example, an HIV viral sequence with flanking human integration sites may be annotated as HIV and may cause erroneous matches and identification of potential pathogens. As such, embodiments are directed at filtering these "erroneous" reference genomes using a filtering algorithm.

Accordingly, embodiments of the present invention can be applied after a sequencing alignment analysis to help filter, categorize, and interpret the results of the sequencing analysis to identify a smaller list of potential pathogens to a more manageable and easily interpretable result. Thus, embodiments may be directed at filtering results once a system has the raw reads, raw contigs, and assembled contigs are determined. Embodiments can take the reads and annotate them with what the hits were from the alignment analysis. For example, the system may take the results of the analysis and determine how accurate and/or good of a hit a result is. The system can take that annotated raw output and further filter it to remove mis-annotated results and false positive aligned reference genomes. Generated result tables showing the alignments and the coverage maps can be determined and displayed after filtering.

A. Filtering Method

Figure 5:
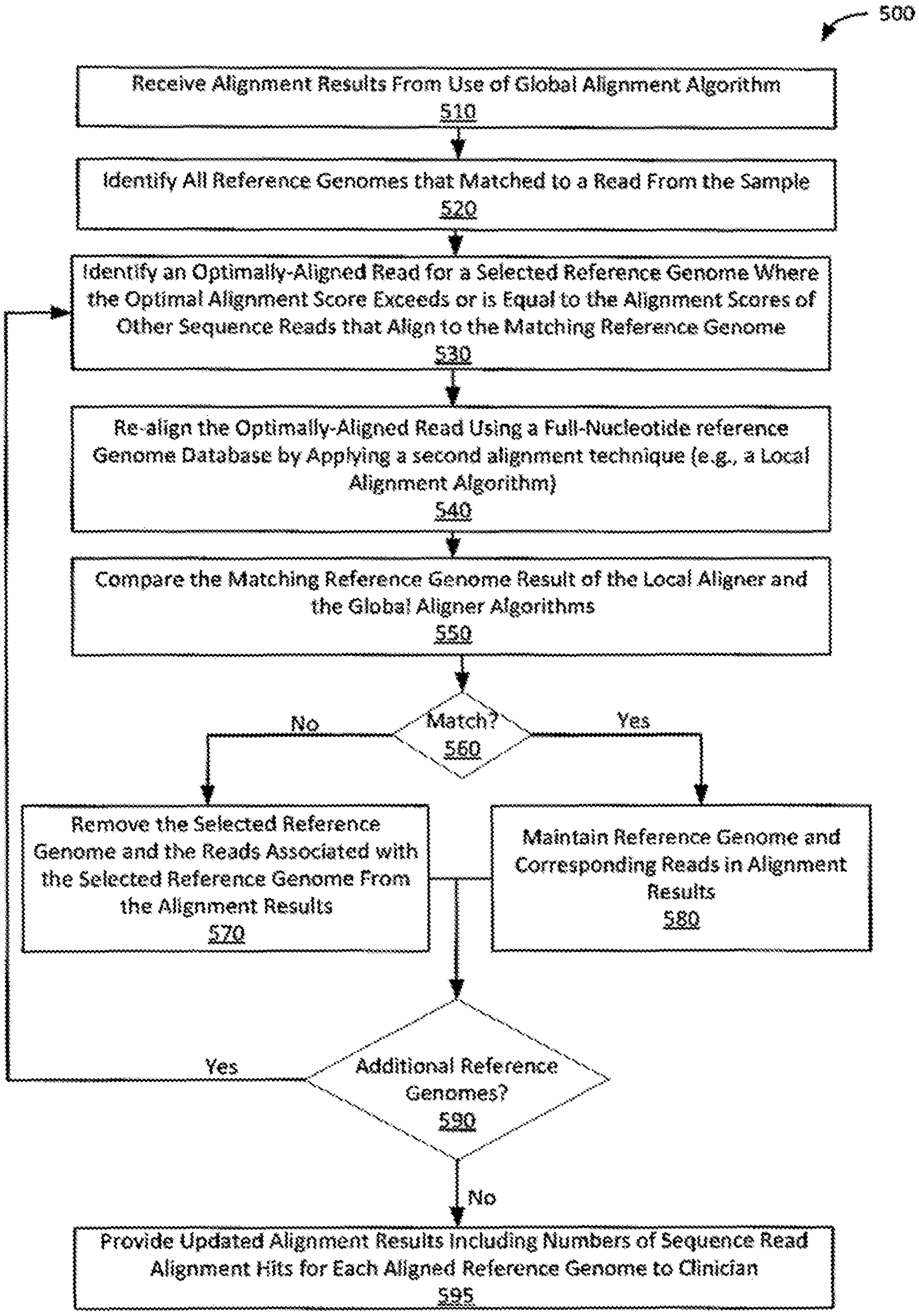
FIG. 5 shows an exemplary method of filtering the results of an alignment process to one or more classified reference genome databases for sequence reads of a sample according to embodiments of the present invention.

FIG. 5 shows an exemplary filtering process 500 for removing false-positive and/or other erroneous reference genome sequences from alignment results. Before the process shown in FIG. 5, the system may receive a plurality of sequence reads obtained from a sequencing of DNA molecules from a sample of biological material that includes multiple different organisms. In some embodiments, the alignment results may have been previously taxonomically classified, e.g., using process 400.

At step 510, alignment results are obtained in response to applying an initial alignment technique (e.g., using a global alignment algorithm) to a plurality of sequence reads from a sample to align the sequence reads to reference genomes in a global database. The alignment results include a matching reference genome for each of at least a portion of the sequence reads in the sample that the sequence read aligns. For example, the alignment technique may include a global alignment algorithm that takes each sequence read and searches a database of classified reference genomes for aligned portions of the sequence reads to portions of the classified reference genomes. The results may include multiple aligned reference genomes for each of the reads, and each reference genome sequence may have many different reads that align to a portion of the reference genome.

The alignment results may include a plurality of sequence reads, sequence read identifiers, a plurality of aligned classified reference genomes, reference genome identifiers from the database of reference genomes, an alignment and/or similarity measurement for each of the alignments, a taxonomy identifier and/or other classification information associated with each of the reference genomes, and any other suitable information that may be used in alignment and identification processes. For example, the source and/or database identifier where the aligned reference genome was stored, the source where the reference genome was provided from (e.g., hospital, clinic, company, provider, etc.), and the data and/or time of the upload may also be provided.

FIG. 6 shows an exemplary summary 620 of sequence alignment results for three different samples. Column 610 shows read type. The first sample 630 and second sample 640 are known to be entrovirus D68, and the third sample 650 is a control that aligns with hepatitis C. The three samples shown in FIG. 6 include a result table that shows the number of initial sequence reads (e.g., for sample 1 there are 2,159,196 sequence reads), the number of sequence reads after preprocessing (e.g., for sample 1 the preprocessing results in 1,933,046 sequence reads), the number of sequence reads that align to human reference sequence genomes (e.g., for sample 1, 1,725,425 reads align to human reference sequence genomes), the number of reads that matched to a reference genome (e.g., for sample 1, 133,932 reads aligned with a reference genome from the database of reference genomes), and the number of bacteria and viruses matched (e.g., 133,827 and 21, respectively for sample 1). Further, the sequence statistics shows the percentage of human matches (e.g., 89.3% for sample 1) and the percentage of reads that remained after preprocessing (e.g., 89.5% for sample 1).

Additionally, FIG. 7 shows an exemplary result table 700 for initial sequence reads. The result table includes the multiple reference genomes that matched with at least one sequence read, a taxonomic identifier for each reference genome including a species (710), genus (720), and family (730) classification for each reference genome. The species, genus, and family classifications are hierarchical with the species level being the lowest level, the genus level being above the species level, and the family level being above both the species and the genus level. The taxonomic identifier and the corresponding classification information may be provided by the classification information (e.g., an annotation entry) of an aligned reference genome from the database that was used during alignment.

Further, the results table may include tag (740) for each reference genome that may identify the database that the reference genome was aligned with and the type of reference genome (e.g., human, plant, bacteria, etc.). Finally, the result table may include the number of reads that aligned to each reference genome for each sample. For example, for the first sample (column 750) shown in FIG. 7, there are 133,004 reads aligned to Enterovirus D; 247 reads aligned to Enterovirus sp., 574 sequence reads aligned to Human Enterovirus, 1 read aligned to human enterovirus K1105_171204, and 1 read aligned to human rhinovirus sp. Accordingly, initial alignment results may include any alignment matches to any of the reference genomes that are present in the database. The second sample (column 760) has a similar pattern as for the first sample 750. The negative control (column 770) shows a match for hepatitis C, as is expected.

At step 520, the system identifies all reference genomes that matched to a read from the sample. For example, for the alignment results of sample #1 shown in FIG. 7, five different reference genomes were aligned with sequence reads from the sample.

At step 530, the system identifies an optimally-aligning sequence read that aligns to the matching reference genome with an optimal alignment score that exceeds or is equal to alignments scores of other sequence reads that align to the matching reference genome. The optimally-aligning sequence read arid optimal alignment score can be identified based on the initial alignment results. The optimally-aligned sequence read may be determined by analyzing the reads that aligned with the reference genome and comparing their alignment value for the closest match. Any process may be used to identify the best match, for example, the read with the most significant match may be defined in SNAP by minimum edit distance and RAPSearch by minimum e-value.

At step 540, the system applies a second alignment technique for the optimally aligning sequence read to the plurality of classified reference genomes to obtain a plurality of new alignment scores. The second alignment technique may include a different alignment technique, a different reference database, and/or a combination thereof. For example, a local alignment algorithm may be applied for the second alignment technique that may take longer to process for each sequence read but because there are fewer sequence reads to process (e.g., only the identified optimally-aligning sequence reads from step 530), the processing time may not overly delay the identification process.

For example, the first alignment technique may include a global alignment algorithm (e.g., SNAP/RAPSearch) that provides faster analysis, but may be sensitive to poor quality sequence regions. The second alignment technique may include applying a local aligner (e.g., BLASTn, Bowtie2, etc.) that may be much slower (1,000×-10000× slower), but that is less sensitive to poor reads and may provide a different alignment of the sequence read that can be compared to the results of the first alignment technique. Thus, the use of the two different alignment techniques allows the system to correct rare "false positives" that occur from the first alignment technique (e.g., SNAP alignment). By only selecting one "test hit" read per reference genome for the second alignment technique (e.g., BLASTn confirmatory alignment), the system can greatly speed up the turnaround time of the process.

At step 550, the system compares the re-alignment results obtained using the second alignment technique for the optimally-aligned read with the initial alignment results obtained using the first alignment technique. For example, different reference genomes may be aligned with the sequence read using the second alignment technique that were not aligned and/or different alignment scores may be returned with the re-alignment than the original alignment.

At step 560, the system determines whether the alignment results using the first alignment technique match the alignment results using the second alignment technique. The comparison of the first alignment results and the second alignment results to determine a match may be accomplished through any suitable manner. For example, the system may determine whether any of the new alignment scores exceeds the optimal alignment score for the optimally aligning sequence read. In other embodiments, the system may determine whether the same reference genome was aligned with the sequence read. Further, other embodiments may determine whether the aligned reference genome sequences share the same taxonomic identifier (e.g., the two reference genome sequences share the same family, genus, and species classifications).

At step 570, if the alignment results for the sequence read are determined not to match, the system may remove the reference genome sequence from the results and all corresponding sequence reads that aligned with the reference genome sequence. In some embodiments, if a sequence read aligned with multiple different reference genomes, only the association of that read with the currently analyzed reference genome sequence may be removed and the read itself (along with the alignment result to the other reference genome sequence) may not be removed. Thus, for the exemplary comparison method of comparing the alignment scores discussed above, when one new alignment score exceeds the optimal alignment score for the optimally aligning sequence read, the system may remove the matching reference genome from the set of matching reference genomes and the corresponding sequence reads associated with the reference genome. In some embodiments, if the two reference genomes share a same taxonomic identifier, the matching reference is not removed.

For example, FIGS. 7-8 shows a table of example results where filtering has been applied to remove mis-annotated and false positive alignments. FIG. 7 shows the raw initial alignment results and FIG. 8 shows the results 800 after filtering has been applied. As shown in FIG. 8, the effect of filtering is to remove two mis-assigned reads that occur as a result of misannotations in the database (761 and 771). These reads are annotated as "hepatitis B" and "simian virus 40" but actually are human integration sites that have been mis-annotated as viral. Using a local aligner (e.g., BLASTn), the system determined that these two reads are actually human reads (returning human reference genomes), and are therefore removed from the output when the alignment results do not match with the initial alignment results of "hepatitis B" and "simian virus 40".

At step 580, if the alignment results for the sequence read are determined to match, the system may consider the reference genome a real match that is not mis-annotated and may maintain the reference genome and aligned sequence reads in the alignment results.

At step 590, the system determines whether all of the reference genomes have had the filtering process applied. If there are additional reference genomes to be analyzed, the system may repeat the process for the next aligned reference genome in the initial alignment results (and may return to step 530). This process may continue until all of the aligned reference genomes have been analyzed for false-positive matches and are removed and/or confirmed as matches.

At step 595, once the system has applied the filtering process to all of the aligned reference genomes, the process may provide the updated alignment results (e.g., not including the selected reference genomes from step 570) to the sample alignment system for display to an operator/clinician. In some embodiments, just the set of matching reference genomes is output. In some embodiments, additional processing may be applied to the updated alignment results before returning the updated alignment results to the sample analysis computer, as described herein.

Accordingly, embodiments may apply a filtering algorithm to the results that identifies all the false positive hits, and systematically remove false positive hits corresponding to that genome. The system can identify the particular genomes that provided a sufficient quality alignment. The system can then further analyze those reads to remove further alignments that do not appear to be high quality. The filtering algorithm can apply an even more stringent criteria to remove hits that are likely not real and instead are due to a misannotation of a reference genome database and/or a misclassification.

For example, a particular read might have hit two, five, or more hits. If a genome had a single hit then it is likely an accurate hit, but if a read hit ten different reference genomes, then it is not likely that the hit is of a high quality. Thus, the filtering could remove all those hits and a new summary table and/or coverage map for the genome. Further, if the coverage map for a particular genome has now drastically reduced due to removing the false positive hits, then the system may remove the genome as a potential pathogen or cause of the illness. Accordingly, embodiments of the present invention may filter what was fifty results (e.g., fifty different bacteria) down to the five bacteria that are the most high quality and likely real results. This allows for much easier and faster clinical analysis and/or interpretation.

In some embodiments, methods 400 and 500 can be combined in a single pipeline, e.g., in a research pipeline. In other embodiments, method 500 may not be performed, e.g., a clinical pipeline might not include method 500. For example, the taxonomic classification may be sufficiently accurate that filtering may not be needed. And, such a pipeline can operate faster without the filtering step, particularly one that uses BLASTn. The turnaround time for a clinical pipeline may be desired within 4-6 hours, whereas more time is acceptable for a research pipeline. Thus, filtering, RAPSearch translated nucleotide alignment, and contig assembly may be retained in a research pipeline, but dropped for a clinical pipeline.

B. Ribosomal RNA Sequence Removal

Additionally, in some embodiments, ribosomal RNA sequences may be removed from the alignment results. Sequences derived from ribosomal regions are difficult to speciate/classify accurately due to conservation of the ribosomal sequences. Accordingly, embodiments may remove ribosomal sequences from the alignment output by aligning sequence reads that had been assigned to bacteria against bacterial ribosomal 16S/23S reference genome sequences. Additionally, the aligned sequence reads assigned to eukaryotes (fungi and parasites) may be further aligned to 18S/28S GIs. Any sequence reads that align to these bacterial or eukaryotic ribosomal reference genomes may be removed from the alignment results.

C. "On-the-Fly" Annotation of Database of Classified Reference Genomes: Automated Clean-Up of the Reference Database Further, due to the rapidly expanding number of reference genomes stored in the classified reference genomic sequence database, such databases may double every 3 years or faster. However, there are very few controls over who or the quality of those providing reference genomic sequences. Accordingly, embodiments can includes automated scripts to (1) download all sequences from the GenBank (currently ~72 GB of data), (2) remove all entries that are poorly annotated by screening out key words in the description of a reference genome sequence entry (e.g., "uncultured", "unclassified", "environmental"), (3) remove all vector sequences, and (4) chop up the classified reference genome sequence database (e.g., GenBank) into "chunks" and convert them into reference databases to be used by local and global alignment algorithms (e.g., SNAP and RAPSearch). A database may be chopped up so as to fit into memory.

V. Removal of Background

As mentioned above, a negative control can be used to identify contaminants or other microorganisms that are not clinically relevant. Such remove of background microorganisms is particularly relevant to clinical applications, where diagnosis and treatment of a patient are a goal. Embodiments can provide one or more criteria for discriminating between a pathogen and a contaminant.

In some embodiments, one or more control samples can be analyzed in parallel (simultaneously) with one or more patient samples (e.g., 5-8 patient samples). A positive control can consist of several different organisms spiked into negative matrix, e.g., spinal cord fluid. A negative control sample (also a called a no-template control) has no spiked organisms. The negative control can be just the buffer that is used for a PCR reaction, which is part of the library preparation for sequencing.

A. Types of Controls

The positive control can be used to confirm that the microorganisms in the spiked contamination are identified. The positive control can ensure that the procedure is robust. For instance, if the sample is like a bloody fluid, the heme in blood may actually inhibit PCR. There can be a negative result, but it might be a false negative. Thus, if the positive control is negative, then the sample can be identified as a false negative. The external positive control can ensure that there are a certain number of reads for each of the spiked organisms (e.g., 7 different organisms), in order for the run to pass quality control.

With the no template control (e.g., a buffer for a PCR reaction or other library preparation step), any reads classified (i.e., hits) as aligning to a microorganism can be identified as corresponding to background. As examples, such false hits can correspond to: reagent contamination, contamination introduced in a laboratory, or contamination introduced from other samples (cross-contamination). In this manner, the number of hits can be reduced, and proper treatment for an actual pathogen is more likely to be performed.

An internal spiked control can include organisms spiked into a patient sample. For example, a DNA phage and/or an RNA phage can be spiked in specific concentrations in a clinical sample. Embodiments can check to make sure that the phages can be detected in the DNA library, e.g., a sufficient number of sequences from the DNA phage. Similarly, a check can make sure that the phages are detected in the RNA library, e.g., a sufficient number of sequences from the RNA phage. This control can be an internal control on every sample, in addition to external control.

B. Normalization

After analyzing the data from the sequencing of the samples (e.g., aligning, classifying, filtering), a list of potential candidate pathogens can be obtained. The list can be a table showing a number of reads seen for each of a plurality of species or other taxonomic classification. The number of reads can be normalized. For instance, the number of reads can be determined per million reads. If there are 10 hits and 10 million reads, the RPM (reads per million) will be one. The total reads can be raw reads that were generated per clinical sample. But, there can be further normalization.

An RPM can also be determined in the negative control. An RPM ratio can be determined from the reads per million (i.e., of a particular taxonomic classification) in the sample divided by your reads per million in the negative control. For example, assume there are 10 normalized reads for a virus HIV) in the sample, and two normalized reads in the no-template control. In that case, the RPM ratio would be five. If there are no reads in the negative control, then there would be a division by zero error. In such cases, a value of one can be used as the RPM from the NTC sample. In other words, the RPM ratio can be the reads per million in the sample.

The RPM ratio allows for easier discrimination of what is really in the sample and what is background. A threshold (e.g., 10) can be used for the discrimination. Thus, pathogens with an RPM ratio of greater than 10 can be identified as clinically significant. Using this criteria, very good sensitivity and specificity can be obtained. The use of the RPM ratio reduces the number of false positive. In particular, very good test performance is obtained relative to using the Bayesian probability, which is based on just the number of reads in a sample. Such probabilistic method can be used when determining an error model, and do not involve normalization from reads in a negative control.

Tables 1-4 below shows revised accuracy data with and without discrepancy testing for results-based and sample-based testing. Discrepancy testing refers to the use of an orthogonal (i.e. different kind of) test to resolve discrepant results between the mNGS assay and conventional clinical microbiology laboratory testing. For instance, if a sample is found to be positive for *Mycobacterium tuberculosis* by mNGS but is negative by culture (because some *Mycobacterium tuberculosis* strains grow slowly or not at all in culture depending on pathogen titer and sample type), a *Mycobacterium tuberculosis* PCR test can be used as an orthogonal test for discrepancy testing, and the results of the orthogonal test are taken as correct for the purposes of determining accuracy.

For sample-based testing, for each sample, performance is evaluated only as it pertains to detection of the original organism reported by the reference lab. For samples completely negative by reference lab testing, the ability to detect all 5 organism types is evaluated.

For result-based testing, for each sample, performance is evaluated as it pertains to detection of all 5 organism types (bacteria, fungi, DNA virus, RNA virus and parasites). Only results for acceptable samples (passed quality control metrics of >5,000,000 reads per library and >10 RPM of either an internally spiked DNA control, T1 bacteriophage, for DNA libraries, or an internally spiked RNA control, M2 bacteriophage, for RNA libraries; sufficient sample volume) are provided in the tables below.

Table 1 shows sample-based accuracy (most clinically significant result per sample) without discrepancy testing.

TABLE 1

Sample-based accuracy (most clinically significant result per sample)

| | | ClinMicro Reference Lab | | | |
|---|---|---|---|---|---|
| | Total | Pos | Neg | Untested | Total |
| mNGS | Pos | 59 | 7 | 7 | 73 |
| | Neg | 25 | 90 | | 115 |
| | Total | 84 | 97 | 7 | |
| Sensitivity | TP/(TP + FN) | 70.2 | | | |
| Specificity | TN/(TN + FP) | 92.8 | | | |
| Accuracy | (TP + TN)/<br>(TN + FN + FP + FN) | 82.3 | | | |

Table 2 shows results-based accuracy (includes multiple positive i negative results per sample) without discrepancy testing.

TABLE 2

Results-insect accuracy (includes multiple positive/negative results per sample)

| | | ClinMicro Reference Lab | | | |
|---|---|---|---|---|---|
| | Total | Pos | Neg | Untested | Total |
| mNGS | Pos | 60 | 7 | 31 | 98 |
| | Neg | 27 | 404 | | 431 |
| | Total | 87 | 411 | 31 | |
| Sensitivity | TP/(TP + FN) | | 69.0 | | |
| Specificity | TN/(TN + FP) | 98.3 | | | |
| Accuracy | (TP + TN)/<br>(TN + FN + FP + FN) | | 93.2 | | |

Table 3 shows revised sample-based accuracy after discrepancy testing.

TABLE 3

Revised accuracy after discrepancy testing, sample-based

| | | ClinMicro Reference Lab | | | |
|---|---|---|---|---|---|
| | Total | Pos | Neg | Untested | Total |
| mNGS | Pos | 68 | 7 | 22 | 97 |
| | Neg | 11 | 327 | | 338 |
| | Total | 79 | 334 | 22 | |
| Sensitivity TPR | TP/(TP + FN) | 86.1 | | | |
| Specificity TNR | TN/(TN + FP) | 97.9 | | | |

Table 4 shows revised results-based accuracy after discrepancy testing. Only results for acceptable samples are provided.

TABLE 4

Revised accuracy after discrepancy testing, results-based

| | | ClinMicro Reference Lab | | | |
|---|---|---|---|---|---|
| | Total | Pos | Neg | Untested | Total |
| mNGS | Pos | 47 | 6 | 18 | 71 |
| | Neg | 8 | 303 | | 311 |
| | Total | 55 | 309 | 18 | |
| Sensitivity TPR | TP/(TP + FN) | 85.5 | | | |
| Specificity TNR | TN/(TN + FP) | 98.1 | | | |

After discrepancy testing and including results passing IC with sufficient sample volume, overall sensitivity increases to 86.1% (sample-based) and 85.5% (results-based), while maintaining high specificity. Given the difficulty making an etiologic diagnosis in many cases of encephalitis/meningitis, a test sensitivity of 80-90% with specificity >95% is very useful in patient management decisions. He above data shows that the overall test accuracy is acceptable for clinical use.

The tables can be displayed in a visualization program. The tables can be provided in a user interface, in a normalized or non-normalized manner. A normalized table is easier to identify pathogens than to look at a list of hundreds of hits. For example, many hits can be removed after normalization to obtain the RPM ratio, and use of a threshold.

C. No-Template Control Database

In addition to the use of the no-template control for a given experimental run, embodiments can use a database of no-template controls (NTC database). For every run, the database can be reviewed before a call is made about a pathogen being in the sample, e.g., to make sure that organism is not in the NTC database. The NTC database includes historical data about what pathogens were identified in NTC samples, e.g., within a specific amount of time, such as 30 days.

For example, a herpes virus might be identified in an NTC sample a month ago (e.g., due to contamination resulting from the same lab doing herpes virus testing). Herpes virus 1 is a common cause of meningitis, and thus can be a dangerous pathogen, if it actually existed. The NTC database can include herpes virus 1, until it is not seen in an NTC sample for at least 30 days. In some embodiments, if the taxonomic classification is found on the skin like poly papilloma viruses, they can be excluded outright. But, they can still be included as part of the NTC database.

Very often, background includes skin flora. For instance, papilloma viruses may be seen in clinical samples in the no-template control. If we do see such a virus in a no-template control, it is added to the database. Embodiments may not actually report organisms that were found in the no-template control unless they are present at a much higher level. For example, assume the RPM was 10 in the NTC for one run, then the taxonomic classification gets added to the database with an RPM of 10. For the next run, if there was a herpes virus detected at 10 RPM (i.e., an RPM ratio of 1), it would not be reported when a threshold of greater than 10 for the RPM ration was used. It would have to be at an RPM of 100 to provide an RPM ration of 10 times the highest level that was present in the NTC database.

As it is not desirable to keep these pathogens in the database because that would affect the performance of the test, as the NTC database decreases the sensitivity, since the bar is set higher to make a positive call for the pathogens in the NTC database. Thus, the NTC database is an evolving database. For example, if a pathogen has not been present for longer than three months (or other specified time period), it then gets removed from the database. Steps can be performed to remove contaminants from NTC samples, e.g., replacing reagents. The amount (e.g., RPM) in the NTC database for a particular contaminant can be updated from the initial value to a new value if the new value is greater than the initial value. Accordingly, in one embodiment, the amount in the NTC database for a contaminant can be the maximum that is observed.

D. Flowchart for Use of NTC

Figure 11:
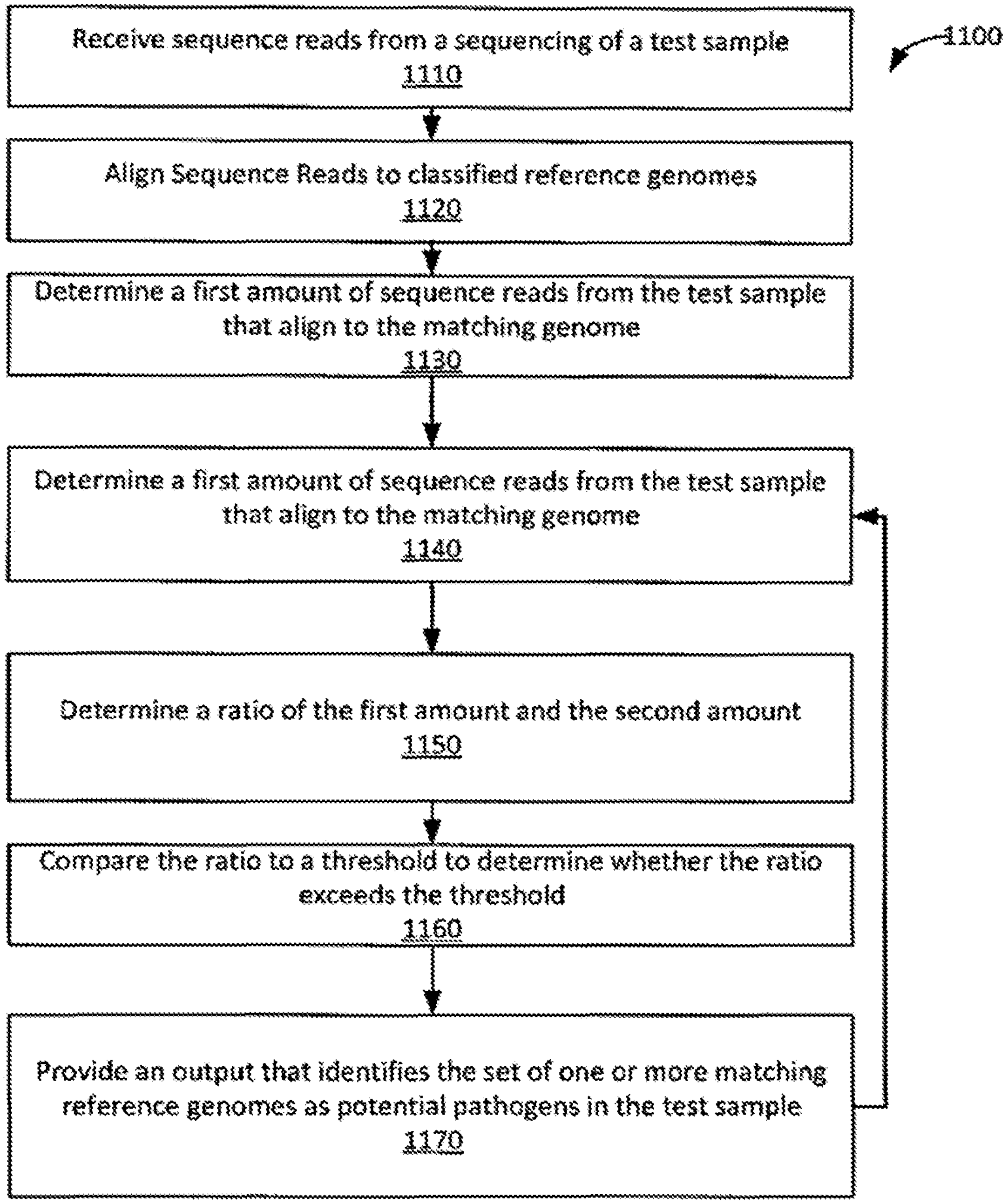
FIG. 11 is a flowchart of a method for identifying pathogens in a test sample of biological material according to embodiments of the present invention.

FIG. 11 is a flowchart of a method 1100 for identifying pathogens in a test sample of biological material according to embodiments of the present invention. Method 1100 may be performed by a computer system. The test sample includes DNA molecules from a plurality of organisms, e.g., from a patient and from microorganisms.

At block 1110, a plurality of sequence reads are obtain from a sequencing of DNA molecules from the test sample of biological material. The sequence reads can be received at the computer system in a variety of ways, e.g., via a network or a removable storage device. The computer system can also receive information about sequence reads from a negative control sample. For example, the computer system can receive an amount of sequence reads for a plurality of difference reference genomes, e.g., as classified into various taxonomic levels.

At block 1120, an alignment technique is used to align the plurality of sequence reads to a plurality of classified reference genomes in a database. The reference genomes may be considered classified in that the genomes are classified to at least one classification level in a taxonomy. Alignment results can include, for each of at least a portion of the sequence reads, at least one matching reference genome to which the sequence read aligns. The alignment results can include classification information for each of the matching reference genomes.

Blocks 1130-1160 may be performed for each of a group of one or more matching reference genomes.

At block 1130, a first amount of sequence reads from the test sample that align to the matching genome is determined. As an example, the first amount may be a total number of sequence reads aligned to the particular matching reference genome. The first amount may be normalized based on the number of sequence reads obtained from the test sample, or the total number of sequence reads aligned to at least one reference genome At block 1140, a second amount of sequence reads from a negative control sample that align to the matching genome is determined. In one embodiment, the second amount of sequence reads can be determined from a negative control database. In another embodiment, the second amount of sequence reads can be determined from a parallel sequencing of a negative control sample. Amounts from a parallel negative control sample and the negative control sample can be combined to provide a single amount.

At block 1150, a ratio of the first amount and the second amount is determined. The ratio can take various forms, such as the first mount divided by the second amount, or the second amount divided by the first amount. Further, a numerator or denominator can include a sum of the two amounts.

At block 1160, the ratio is compared to a threshold to determine whether the ratio exceeds the threshold. A set of one or more matching reference genomes can have the ratio exceed the threshold. The threshold can be determined based on empirical data (e.g., values of samples with a known composition), as will be appreciated by one skilled in the art. The selection of the threshold can be based on a desired balance between sensitivity and specificity.

At block 1170, an output is provided that identifies the set of one or more snatching reference genomes as potential pathogens in the test sample. As examples, the output can be a list of the set of matching reference genomes, e.g., presented in classification levels. Such a list could include more matching reference genomes, where the set is indicated, as may be done with a marker or the ratio. For instance, an RPM ratio can be provided.

VI. Further Data Analysis

Once the false-positives and inaccurate reads have been removed, the system may apply post-filtering analysis and provide the results to the sample analysis system for display the clinician. In some embodiments, the filtered and classified results may be used to generate new coverage maps. The filtered and classified results may be analyzed to determine a best match and whether a sufficient match obtained. For example, a best match score (or any one of the individual score) can be required to be above a specified threshold. In some embodiments, if the coverage is below a certain level, than the system will dismiss the organism as being a possibility. In other embodiments, all possible identification results could be provided to allow a clinician to make an identification.

Further, in some embodiments, a best match algorithm may be applied to select, for instance, the best match among a variety of closely related matches. For instance, the results may have hits to multiple different strains of influenza. The best match algorithm may choose the most closely matched sequence in the reference database and select that classified element as the best match for the sample sequence.

Examples of a best match algorithm are described herein, e.g., in section II.C. In another example, for each species, the reference genome sequence with the greatest number of reads assigned to it can be used as a reference for mapping of all of the species-specific reads. A "consensus sequence" may be generated from the mapping. The global pairwise identity using the Needleman-Wunsch algorithm may then calculated between the "consensus sequence" and each reference genome sequence. The reference genome sequence with the greatest global pairwise identity may be selected as the top reference genome sequence. The reference genome sequences under consideration can also be prioritized as follows: (1) complete genomes, (2) complete sequences, or (3) partial sequences/individual genes."

A positive pathogen identification may be reported where for each top reference genome a positive identification metric may be evaluated and provided to the clinician in a return message to the sample analysis computer. For example, the positive identification metric may include coverage of at least 3 genes/open reading frames (ORFs), or where there are fewer than 3 ORFs in the virus, then coverage that exceeds greater than 3 times the read length (e.g., for 100 bp sequencing, coverage of greater than 300 bp).

Additionally, systems may implement a tagging mechanism for the reference genomes that are matched to the sample sequence reads in order to make pathogen identification easier. For instance, the system may add the "host" to viral reference genome sequences (GIs), where the "host" is bacteria, for instance, the system knows that the virus is a phage (which the system may want to mask out sequences to phages). Similarly, the system can apply arbitrary labels such as "pathogens", "colonizers", and "laboratory contaminants" to specific bacterial GIs that can be helpful in downstream visualization of results for clinical interpretation. These results may be provided with the final results of the alignment, filtering, and classification process.

VII. Example for Neurobrucellosis

A diagnosis of brucellosis can be difficult because routine culture and serological methods exhibit variable sensitivity and specificity. At present, the standard laboratory diagnosis of brucellosis is based on isolation of the bacteria from clinical specimens and/or serological detection of *Brucella* antibodies.

Neurobrucellosis is a known complication of systemic *Brucella* infection. It remains a difficult diagnosis to make and can mimic other fastidious infections such as TB [1]. Manifestations of neurobrucellosis are widely variable and include meningoencephalitis, cerebrovascular disease, peripheral and cranial neuropathies, or myelitis. Neuroimaging studies of neurobrucellosis can also vary greatly among individuals [6]. A previous study from Turkey reported a high prevalence of neurobrucellosis at 37% among 128 patients with brucellosis. Although culture is the gold standard for diagnosis, *Brucella* species are relatively fastidious and slow-growing; cultures fail to recover the organism 30-90% of the time, and also present a risk of laboratory-acquired infection [7]. Serology is more sensitive for detection, but can lead to false-positive results and may not distinguish between active and prior infection.

Molecular methods based on detection of nucleic acid such as PCR [8] and now potentially metagenomic NGS [13] can offer increased sensitivity and specificity over conventional diagnostic testing. We present the use of a metagenomic next-generation sequencing assay to diagnose a case of neurobrucellosis from cerebrospinal fluid (CSF), resulting in the institution of appropriate antibiotic treatment and a favorable clinical outcome.

A. Case Report

Initially, microbiological testing was positive for Epstein-Barr virus (EBV) and human herpesvirus 7 (HHV-7) from CSF. Testing for other pathogens, including *Brucella* by IgM antibody, was negative. The patient was treated with parenteral acyclovir, followed by oral ganciclovir to complete a 14-day course. Two weeks after hospital discharge, she developed back pain and worsening headache. Upon hospitalization, the patient's vital signs were normal without fever. Physical examination was remarkable for multifocal myoclonus throughout her body. There was hyperreflexia and decreased proprioceptive sensation of bilateral lower limbs. A complete blood count was notable for a white blood cell count of $4.82\times10^9$/L (44% neutrophils, 44% lymphocytes, 10% monocytes).

A repeat lumbar puncture was performed, with additional microbiological testing unrevealing. Cytologic examination of the CSF revealed no malignant cells. Despite a negative tuberculin skin test and QuantiFERON-TB test, she was started on 4-drug therapy with isoniazid, rifampin, pyrazinamide, and ethambutol given a high concern for TB disease based on the patient's suggestive CSF profile and risk factors for TB.

On day 8 of hospitalization, the result of CSF for *Mycobacterium tuberculosis* (MTB) by PCR was negative. Given the lack of response to empiric TB therapy, there was a concern for drug-resistant TB. Ethambutol was thus changed to ethionamide, and levofloxacin was added to the regimen. She improved substantially after changing her antibiotic regimen, and was discharged home on 5 anti-TB medications. At follow up 1 week and 1 month after discharge, her headache had resolved, but she continued to have fatigue, mild back pain, and intermittent episodes of shaking of her extremities. When the result of the mycobacterial culture was finalized as negative at 6 weeks, she returned to Mexico to continue her anti-TB therapy with INH and rifampin alone.

B. Results

RNA and DNA mNGS libraries from 600 μL of the patient's CSF sample were constructed. From a total of 23,638,587 raw reads in the DNA library, there were 277 (0.0012%) reads corresponding to the *Brucella* genus in the DNA library, corresponding to an RPM ratio of 15.6, with all species-specific reads aligning to *Brucella melitensis* (see Tables 1200 of FIG. 12, 1300 of FIG. 13, and 1 and 2 of the Appendix). Notably, no reads aligning to *Brucella* among 9,161,626 reads in the corresponding RNA library from CSF were detected, and *Brucella* reads were absent in both negative "no template control" (NTC) and positive control samples. Other bacterial reads present in DNA library were also present in the NTC sample processed in parallel on the same run, and thus did not meet the established threshold for reporting using an RPM ratio of 10 and were attributed to laboratory reagent contamination.

Similarly, no viruses, fungi, or parasites met criteria for reporting. In contrast, all 7 microorganisms in the positive control were detected at levels above the established reporting threshold. Importantly, no *Brucella* isolates or positive clinical samples from suspected or confirmed cases had been present in the clinical laboratory prior to the mNGS testing, nor had *Brucella* sequences ever been detected in the NTC. The presence of *Brucella* in the patient's cerebrospinal fluid was confirmed by *Brucella*-specific PCR testing and Sanger sequencing of the amplicon. The PCR reaction for 177 bp region of *Brucella* IS711 gene was run on a 2% agarose gel. Other samples included: a no-template-control; 7 organism positive control mixture of CMV, HIV, *Streptococcus agalactiae, Klebsiella pneumoniae, Cryptococcus neoformans*; water; and 1 kb Plus DNA ladder (Invitrogen).

After detection of *Brucella* reads in her CSF sample, the patient was contacted and instructed to seek further medical evaluation. She returned to the hospital in Los Angeles for a second admission. Although she had completed INH and rifampin therapy one week prior, she reported persistent back pain, nausea, and fatigue. Repeat MRI of the brain and spine was remarkable, and CSF was normal. A confirmatory serum *Brucella* agglutinin titer was positive at 1:80. Because of persistent symptoms, mNGS and PCR testing showing *Brucella*, and positive confirmatory serology, she was diagnosed with chronic neurobrucellosis and started on targeted therapy with doxycycline and rifampin. Two weeks after starting therapy, she reported that her symptoms had fully resolved. Notably, *Brucella* spp. was not isolated from either CSF or blood culture, nor was *Brucella* DNA detected in CSF submitted for 16S rRNA gene sequencing.

This highlights the clinical impact of mNGS for diagnosis of infections such as neurobrucellosis that are challenging to accurately diagnose and treat. Although initially covered for TB meningitis using antibiotics that partially treat neurobrucellosis (rifampin+/−levofloxacin), the patient continued to be symptomatic and was not placed on targeted therapy for *Brucella* until comprehensive metagenomic sequencing revealed the presence of bacterial DNA in her CSF and neurobrucellosis was confirmed by *Brucella* agglutinin testing.

FIG. 12 shows table 1200 of sequencing statistics according to embodiments of the present invention. Results are shown from both the patient's sample, no template control (NTC), and the positive batch control (PC) sample.

FIG. 13 shows a table 1300 of the number of reads from DNA libraries and RNA libraries aligning to viral sequences according to embodiments of the present invention. Table 1300 shows the number of reads from DNA libraries and RNA libraries aligning to viral sequences. Results are shown from both the patient's sample, NTC, and the PC sample.

In table 1300, the reported viruses are cytomegalovirus (CMV) in the "DNA PC" column and human immunodeficiency virus 1 (HIV-1) in the "RNA PC" column. These are the viruses spiked into the PC sample. No viruses are reported from the patient CSF because human papillomaviruses, part of skin flora and presumed to be a contaminant, are not reported by the mNGS assay.

Supplementary Table 1 of the Appendix shows the number of reads from the DNA library aligning to bacterial sequences. Results are shown from both the patient's sample, NTC, and the PC sample. In Supplementary Table 1, "*" indicates re-classified to a higher taxonomic rank because reads aligned equally well to multiple different organisms that shared the same species, genus or family. The abbreviations are as follows: NTC, no template control; PC, positive control; and CSF, cerebrospinal fluid.

Supplementary Table 2 of the Appendix shows the number of reads from the DNA library aligning to fungal and parasite sequences. Results are shown from both the patient's sample, NTC, and the PC sample. In Supplementary Table 2, "*" indicates re-classified to a higher taxonomic rank because reads aligned equally well to multiple different organisms that shared the same species, genus or family.

Supplementary Table 3 of the Appendix shows bacterial taxa identified by embodiments using an RPM ratio metric for reads shown in Supplementary Table 1. In Supplementary Table 3, "*" indicates re-classified to a higher taxonomic rank because reads aligned equally well to multiple different organisms that shared the same species, genus or family; "#" indicates positive result according to an RPM (reads per million) ratio ≥10, where the RPM ratio=RPM (sample)/RPM(NTC); and "&" indicates reads correspond to the *Streptococcus agalactiae* PC. The abbreviations are as follows: PC, positive control; CSF, cerebrospinal fluid; mNGS, metagenomic next-generation sequencing; and RPM, reads per million.

In Supplementary Table 3, cells that show a positive result by mNGS assay are highlighted in yellow. Under the column designated "DNA PC", the two bacterial species reported at the pre-established threshold criterion of >10 RPM are *Streptococcus agalactiae* and *Klebsiella pneumoniae*, which were spiked into the PC sample. Other positive rows are not reported because they represent either (1) classification at a higher taxonomic rank (genus) or (2) another bacterial species in the same genus (i.e. *Streptococcus suis*) that does not meet the pre-established requirement of having at least 1/10 of the number of RPM corresponding to the predominant species (*Streptococcus agalactiae*) to call a co-infection from at least 2 different species. Under the column designated "DNA Patient CSF", the only bacterial taxa with >10 RPM is *Brucella* genus, which is the reported organism reported in the patient's CSF.

Supplementary Table 4 of the Appendix shows fungal and parasitic taxa identified by embodiments using an RPM ratio metric for reads shown in Supplementary Table 1. In Supplementary Table 4, "*" indicates re-classified to a higher taxonomic rank because reads aligned equally well to multiple different organisms that shared the same species, genus or family; and "#" indicates positive result according to an RPM ratio ≥10, where the RPM ratio=RPM(sample)/RPM (NTC). The abbreviations are: PC, positive control; CSF, cerebrospinal fluid; mNGS, metagenomic next-generation sequencing; RPM, reads per million.

In Supplementary Table 4, cells that show a positive result by mNGS assay are highlighted in yellow. Under the column "DNA PC", the two fungal/parasitic species reported at the pre-established threshold criterion of >10 RPM are *Cryptococcus neoformans, Aspergillus niger*, and *Toxoplasma gondii*, which were spiked into the PC sample. Other positive rows are not reported because they represent classification at a higher taxonomic rank (genus or family).

Supplementary Tables 3 and 4, which are used to interpret and report mNGS results, show the effect of taxonomic classification and normalization using an "RPM ratio" metric in comparison to the NTC in simplifying the clinical interpretation, as compared to Supplementary Tables 1 and 2, respectively.

Of particular relevance for this case, two chronic granulomatous infections, tuberculosis and brucellosis, have not only overlapping clinical or radiographic features but also histologic characteristics in common [10]. As such, misdiagnosis of tuberculosis in patients with brucellosis has been reported in the literature [10]. This matter is further complicated by the fact that neither a negative CSF mycobacterial culture nor tuberculosis PCR-based assay excludes the diagnosis of TB meningitis if the clinical suspicion is high. Additionally, false-positive *Brucella* seroreactivity, ELISA and agglutination titer, in patients with active TB have also been reported. In this patient's case, the negative *Brucella* IgM but positive IgG was incorrectly attributed to false-positive *Brucella* seroreactivity in the setting of TB and not to active *Brucella* infection. It is possible that the patient may not have mounted a detectable IgM antibody response, or that *Brucella* IgM levels had waned by the time of hospital admission. Confirmatory agglutinin testing may have been helpful in making the diagnosis of *Brucella* earlier.

This patient had temporary clinical improvement after initiation of anti-TB medications. Rifampin and levofloxacin are two anti-TB agents that are also active against *Brucella* spp. [1]. However, rifampin, while active against *Brucella*, should always be used in combination with other agents (e.g. doxycycline, trimethoprim-sulfamethoxazole, or quinolones) since monotherapy, as was inadvertently administered to this patient initially, has been associated with high relapse rates [1]. In hindsight, the patient's prolonged and indolent course was more likely to be associated with *Brucella*, since more rapid clinical deterioration would have been expected for patients with active TB who are inadequately treated [11]. But, *Brucella* at that time was not high on the differential. It is only after discharge and because of the patient's persistent symptoms that an alternative diagnosis was considered. Taken altogether, knowledge of these pitfalls is essential for clinicians to reduce diagnostic errors.

Metagenomic next-generation sequencing (mNGS) is an emerging approach in diagnostic microbiology with the ability to detect all microorganisms—viruses, bacteria, fungi, and parasites—in a single assay [2, 4, 9, 2, 3]. Here mNGS was used to provide an accurate diagnosis of neurobrucellosis and to guide the institution of targeted therapy, leading to complete resolution of the patient's illness.

C. Implementations Details

1. Metagenomic Library Construction

DNA and RNA metagenomic libraries were constructed from the patient's CSF sample as previously described [2, 3]. After bead-beating using Lysis matrix B (MP Biomedicals, Santa Ana Calif.) at 6 m/s for 30 seconds, total nucleic acid was extracted using the Qiagen EZ1 Viral kit (Qiagen, Valencia Calif.). Half of the nucleic acid from CSF was treated with Turbo DNase (Ambion, Waltham Mass.), followed by reverse transcription of the RNA to cDNA using random hexamers and NGS library preparation using the Nextera XT DNA Library Prep Kit (Illumina, San Diego Calif.). The remaining half was treated with the NEBNext Microbiome DNA Enrichment Kit to enrich for microbial DNA (New England Biosciences, Ipswich Mass.)), followed by Nextera XT library preparation. Dual-indexed, barcoded NGS libraries were quantitated on the BioAnalyzer (Agilent, Santa Clara Calif.) and run on the Illumina HiSeq (1.times.160 bp run).

The patient's CSF sample was processed and sequenced as part of a recently developed standardized operating procedure (SOP) for clinical mNGS testing from patient samples in the University of California, San Francisco (UCSF) Clinical Microbiology Laboratory, a CLIA (Clinical Laboratory Improvement Amendments)-licensed laboratory (Naccache, et al., manuscript in preparation). For each sequencing run, the SOP includes running two external controls: (1) a negative "no-template" control (NTC) sample consisting of elution buffer, (2) and a positive control sample consisting of a quantified mixture of 7 representative pathogens (CMV, HIV, *Streptococcus agalactiae, Klebsiella pneumoniae, Cryptococcus neoformans, Aspergillus niger*, and *Toxoplasma gondii*). Each is spiked into negative CSF matrix at a concentration 1-2 log above the estimated limits of detection for that microorganism by probit analysis (Naccache, et al., manuscript in preparation).

2. Bioinformatics Analysis

Metagenomic NGS data was analyzed for pathogens using a modified version of the SURPI ("sequence-based ultra-rapid pathogen identification") computational pipeline, which identifies pathogen sequences on the basis of nucleotide alignments to National Center for Biotechnology information (NCBI) nt reference database (March 2015 build) [4]. A clinical version of the SURPI pipeline, named SURPI+, which employs taxonomic classification for more accurate read assignments and establish normalized metrics and thresholds for clinical results reporting, was used for automated interpretation. Briefly, for identification of viral sequences, both mNGS data from bath DNA and RNA sample libraries were used, whereas only mNGS data from DNA libraries alone were used for identification of sequences from bacteria, fungi, and parasites. An edit distance cutoff of 16, indicating the number of single nucleotide insertions, deletions, or mismatches allowed between the read and the reference sequence, was used for virus detection, whereas a more stringent edit distance cutoff of 1 was used far bacterial, fungal, and parasitic detection [2, 3]. Following alignment, a rapid taxonomic classification algorithm based on the lowest common ancestor algorithm was used to assign viral, bacterial, and non-chordate eukaryotic (fungal or parasitic) NGS reads to the species, genus, or family level, as previously described [2, 3].

3. Results Reporting

As part of clinical validation of mNGS testing for pathogen detection, we have established threshold cutoffs for automated reporting of positive results (Naccache, et al., manuscript in preparation). Briefly, for reporting of bacteria, fungi, and parasites, the cutoff is defined as an RPM (reads per million) ratio of ≥10, where the RPM ratio is defined as the $RPM_{sample}/RPM_{NTC}$ for any given taxon (species, genus, or family). If the taxon is not present in the NTC, then the $RPM_{NTC}$ is 1. For reporting of viruses, the criteria can include coverage of ≥2 non-contiguous/non-overlapping gene regions. Viruses with non-vertebrate hosts, that are found in the NTC, or that constitute normal body flora (e.g. anelloviruses) are not reported. A "gene region" can be defined as a non-overlapping and non-contiguous region of length<=read length (e.g., 141 bp).

4. *Brucella* PCR Confirmation

Confirmation of *Brucella* detection was performed by PCR using the following primer set targeting the IS711 gene [5]: BrucellaGenus_F-2_GCCTTGGATCTGAGCCGTT (SEQ ID NO:1); BrucellaGenus_IS711_R GGCCTACC-GCTGCGAAT (SEQ ID NO:2). The reaction was carried out using the Qiagen One-Step RT-PCR Kit in a 25 μL total reaction volume by addition of 4 μL Q solution, 4 μL. 5.times. buffer, 1 μL dNTP, 1 μL enzyme, 1 μL of each primer at 12 μmol, and 2 μL of template extracted DNA, and water. Cycling conditions were as follows: 40 cycles of 94° C., 30 s/53° C., 30 s/72° C., 30. The recovered sequence was confirmed to be Bruce by Sanger sequencing of the PCR amplicon.

VIII. Exemplary Computer System

Figure 14:
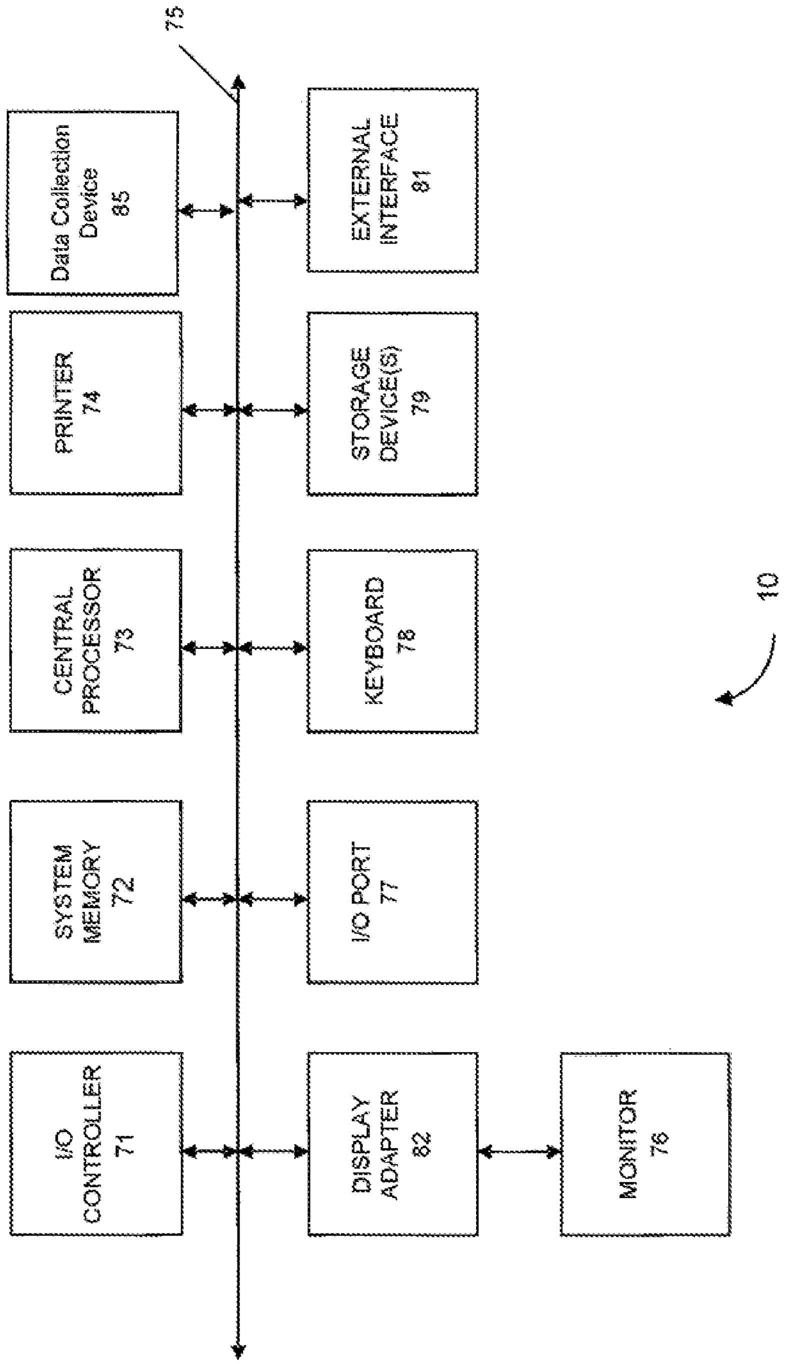
FIG. 14 shows an exemplary computer system.

FIG. 14 shows a block diagram of an example computer system 10 usable with system and methods according to embodiments of the present invention. For example, computer system 10 can be used in implementing sample analysis system 110 and/or sequence identification computer 120.

Any of the computer systems mentioned herein may utilize any suitable number of subsystems. Examples of such subsystems are shown in FIG. 14 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 14 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++. C #, Objective-C, Go, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are herein incorporated by reference in their entirety for all purposes. None is admitted to be prior art. Such references include:

1. Pappas G, Akritidis N, Bosilkovski M, Tsianos E. Brucellosis. The New England journal of medicine 2005; 352(22): 2325-36.
2. Greninger A L, Messacar K, Dunnebacke T, et al. Clinical metagenomic identification of *Balamuthia mandrillaris* encephalitis and assembly of the draft genome: the continuing case for reference genome sequencing. Genome medicine 2015; 7(1): 113.
3. Greninger A L, Naccache S N, Messacar K, et al. A novel outbreak enterovirus D68 strain associated with acute flaccid myelitis cases in the USA (2012-14): a retrospective cohort study. The Lancet Infectious diseases 2015; 15(6): 671-82.
4. Naccache S N, Federman S, Veeraraghavan N, et al. A cloud-compatible bioinformatics pipeline for ultrarapid pathogen identification from next-generation sequencing of clinical samples. Genome research 2014; 24(7): 1180-92.
5. Hinic V, Brodard I, Thomann A, et al. Novel identification and differentiation of *Brucella melitensis, B. abortus, B. suis, B. ovis, B. canis*, and *B. neotomae* suitable for both conventional and real-time PCR systems. Journal of microbiological methods 2008; 75(2): 375-

6. Al-Sous M W, Bolilega S, Al-Kawi M Z, Alwatban J, McLean D R. Neurobrucellosis: clinical and neuroimaging correlation. AJNR American journal of neuroradiology 2004; 25(3): 395-401.
7. Moyer N P H L, Murray P R, Baron E J, Pfaller M A, Tenover F C, Youlken R H. *Brucella*. Manual of Clinical Microbiology. ASM Press, 1995:549-55.
8. Yu W L, Nielsen K. Review of detection of *Brucella* spp. by polymerase chain reaction. Croatian medical journal 2010; 51(4): 306-13.
9. Chiu C Y, Miller S. Next-Generation Sequencing. In: Persing D H, Tenover F C, Hayden R T, Ieven G, Miller M B, Nolte F S. Molecular Microbiology, Diagnostic Principles and Practice, 3rd Edition. Washington, D.C.: ASM Press, 2016:68-79
10. Dasari S, Naha K, Prabhu M. Brucellosis and tuberculosis: clinical overlap and pitfalls. Asian Pacific journal of tropical medicine 2013; 6(10): 823-5.
11. Verdon R, Chevret S, Laissy J P, Wolff M. Tuberculous meningitis in adults: review of 48 cases. Clinical infectious diseases: an official publication of the Infectious Diseases Society of America 1996; 22(6): 982-8.
12. Naccache S N, Peggs K S, Mattes F M, et al. Diagnosis of neuroinvasive astrovirus infection in an immunocompromised adult with encephalitis by unbiased next-generation sequencing. Clinical infectious diseases: an official publication of the Infectious Diseases Society of America 2015; 60(6): 919-23.
13. Wilson M R, Naccache S N, Samayoa E, et al. Actionable diagnosis of neuroleptospirosis by next-generation sequencing. The New England journal of medicine 2014; 370(25): 2408-17.

from the sample of biological material, the sample including DNA or cDNA molecules from a plurality of organisms;

using an initial global alignment technique to align the population of sequence reads to a plurality of classified reference genomes in an electronic database, thereby obtaining alignment results that include, for each of at least a portion of the population of sequence reads, at least one matching reference genome to which the population of sequence read aligns, thereby obtaining a set of matching reference genomes, and wherein the alignment results may further include classification information for each of the matching reference genomes, the classification information including a plurality of taxonomy identifiers;

filtering the alignment results for each matching reference genome of the set of matching reference genomes, by:

identifying an optimally-aligning sequence read that aligns to the matching reference genome with an optimal alignment score that exceeds or is equal to alignments scores of other sequence reads that align to the matching reference genome, thereby obtaining optimally-aligning sequence reads;

for each of the optimally-aligning sequence reads:

applying a second local alignment technique for the optimally-aligning sequence read to the classified reference genomes to obtain a plurality of new alignment scores, wherein the second local alignment technique is at least 1,000 times slower than the initial global alignment technique;

determining whether any of the new alignment scores exceeds the optimal alignment score for the optimally-aligning sequence read;

What is claimed is:

1. A method for identifying one or more pathogens in a sample of biological material, the method comprising, at a computer system:

receiving a population of 1 million or more sequence reads as fasta, fastq, or sam files, wherein the sequence reads are obtained from a sequencing of DNA molecules or reverse transcribed RNA molecules (cDNA)

removing a matching reference genome from the set of matching reference genomes and the corresponding sequence reads associated with the matching reference genome, if the new alignment score exceeds the optimal alignment score for the optimally-aligning sequence read;

identifying a set of the sequence reads that are aligned to two or more of the classified reference genomes with at a least a minimum alignment threshold;

for each sequence read of the set of the sequence reads:
identifying two or more matching reference genomes of the classified reference genomes to which the sequence read aligns with at least the minimum alignment threshold;
assigning a taxonomy identifier to each of the two or more matching reference genomes of the classified reference genomes, thereby obtaining assigned taxonomy identifiers, each taxonomy identifier including at least two levels of classification, the at least two levels having a hierarchy such that there is a lower level and at least one higher level;
comparing the assigned taxonomy identifiers of the two or more classified reference genomes at each of the at least two levels of classification;
removing each level of the at least two levels from the assigned taxonomy identifiers that do not match between the two or more classified reference genomes; and
assigning to the sequence read of the set of the sequence reads a lowest level of the at least two levels of the assigned taxonomy identifiers that is shared between the two or more classified reference genomes; and
providing an identification of one or more taxonomy identifiers based on numbers of corresponding sequence reads;
using sequence reads having an assigned taxonomy identifier to identify the one or more taxonomy identifiers corresponding to the one or more candidate pathogens for each of a set of taxonomy identifiers, by:
determining a total score based on:
at least a coverage of a reference genome and a length of the reference genome corresponding to the taxonomy identifier, and
assigning an identity score corresponding to a fractional sum over genomic positions in the reference genome, the fractional sum of a fraction of sequence reads having an exact match at a genomic position relative to the total number of sequence reads that match or do not match at the genomic position, thereby obtaining total scores for the set of taxonomy identifiers;
ranking the total scores; and
identifying the one or more taxonomy identifiers exceeding a score threshold.

2. The method of claim 1, further comprising:
when none of the at least two levels of the taxonomy identifiers match, associating an unassigned state with the sequence read.

3. The method of claim 1, wherein providing the identification of the one or more taxonomy identifiers corresponding to the one or more candidate pathogens includes providing an amount of corresponding sequence reads.

4. The method of claim 1, wherein the total score for a taxonomy identifier is determined by the equation: (the length+the identity score)×a percent identity score, wherein the percent identity score corresponds to the identity score divided by a number of genomic positions covered by a sequence read aligned to the reference genome.

5. The method of claim 1, wherein the sample of biological material is from a host organism, the method further comprising:
performing a clinical intervention for the host organism based on the identification of the one or more taxonomy identifiers.

6. The method of claim 1, further comprising:
preprocessing the population of sequence reads to perform at least one of:
remove sequence reads identified as low quality sequence reads, and
remove sequence reads identified as low complexity sequence reads.

7. The method of claim 1, wherein the classified reference genomes in the database include reference genomes of microorganisms, the method further comprising:
prior to aligning the population of sequence reads to the classified reference genomes in the database:
aligning the population of sequence reads to a reference human genome; and
removing a portion of the population of sequence reads that align to the reference human genome.

8. The method of claim 7, wherein the classified reference genomes in the database include bacterial genomes, fungal genomes, and viral genomes.

9. The method of claim 1, further comprising:
sequencing DNA molecules from the sample of biological material to obtain at least one million sequence reads, wherein the alignment technique aligns the at least one million sequence reads.

10. A method for identifying pathogens in a sample of biological material, the method comprising, at a computer system:
(i) receiving a population of at least 1 million of sequence reads as fasta, fastq, or sam files, wherein the sequence reads are obtained from a sequencing of DNA molecules from the sample of biological material, the sample including DNA or cDNA molecules from a plurality of organisms;
(ii) using an initial global alignment technique to align the population of sequence reads to a plurality of classified reference genomes in a database, thereby obtaining initial alignment results that include, for each of at least a portion of the sequence reads, a matching reference genome to which the sequence read aligns;
for each of a set of matching reference genomes:
based on the initial alignment results, (iii) identifying an optimally-aligning sequence read that aligns to the matching reference genome with an optimal alignment score that exceeds or is equal to alignments scores of other sequence reads that align to the matching reference genome, thereby obtaining optimally-aligning sequence reads;
for each of the optimally-aligning sequence reads:
(iv) applying a second local alignment technique for the optimally-aligning sequence read to the plurality of classified reference genomes to obtain a plurality of new alignment scores, wherein the second local alignment technique is at least 1,000 times slower than the initial global alignment technique;
(v) determining whether any of the new alignment scores exceeds the optimal alignment score for the optimally-aligning sequence read;
based on one new alignment score exceeding the optimal alignment score for the optimally-aligning sequence read, (vi) removing the matching reference genome from the initial alignment from the set of matching reference genomes and the corresponding sequence reads associated with the matching reference genome;

repeating steps (iii) to step (vi) for each additional reference genome to be analyzed; and providing the set of matching reference genomes.

11. The method of claim 10, wherein the matching reference genome from the initial alignment is removed from the set of matching reference genomes if the matching reference genome shares a same taxonomic level as a reference genome corresponding to the one new alignment score.

12. The method of claim 10, further comprising:

providing the initial alignment results corresponding to the set of matching reference genomes.

* * * * *